(12) United States Patent
Sherley

(10) Patent No.: US 8,759,098 B2
(45) Date of Patent: Jun. 24, 2014

(54) METHOD FOR CLONING PLURIPOTENT STEM CELLS

(75) Inventor: James L. Sherley, Boston, MA (US)

(73) Assignee: Boston Biomedical Research Institute, Inc., Watertown, MA (US)

(*) Notice: Subject to any disclaimer, the term of this patent is extended or adjusted under 35 U.S.C. 154(b) by 0 days.

(21) Appl. No.: 13/513,612

(22) PCT Filed: Dec. 3, 2010

(86) PCT No.: PCT/US2010/058939
§ 371 (c)(1),
(2), (4) Date: Jul. 16, 2012

(87) PCT Pub. No.: WO2011/069091
PCT Pub. Date: Jun. 9, 2011

(65) Prior Publication Data
US 2012/0295351 A1    Nov. 22, 2012

Related U.S. Application Data

(60) Provisional application No. 61/266,602, filed on Dec. 4, 2009.

(51) Int. Cl.
*C12N 5/00* (2006.01)
*C12N 5/02* (2006.01)
*C12N 5/071* (2010.01)

(52) U.S. Cl.
CPC ......... *C12N 5/0696* (2013.01); *C12N 2502/22* (2013.01); *C12N 2500/99* (2013.01); *C12N 2502/13* (2013.01); *C12N 2517/02* (2013.01); *C12N 2500/40* (2013.01)

USPC ............................................ 435/377; 435/325

(58) Field of Classification Search
USPC .................................................. 435/377, 325
See application file for complete search history.

(56) References Cited

FOREIGN PATENT DOCUMENTS

WO    2005121323 A2    12/2005
WO    2007002228 A1    1/2007

OTHER PUBLICATIONS

Kawamura et al, "Linking the p52 tumour suppressor pathway to somatic cell reprogramming", Nature, vol. 460, No. 7259, pp. 1140-1144, 2009.
Takahashi et al, "Induction of Pluripotent Stem Cells from Adult Human Fibroblasts by Defined Factors", Cell, vol. 131, pp. 1-12, 2007.
Sherley, James L., "Asymmetric Cell Kietics Gene: The Key to Expansion of Adult Stem Cells in Culture", Stem Cells, vol. 20, pp. 561-572, 2002.
Pare, J. et al., "Culture Environment-Induced Pluripotency of SACK-Expanded Tissue Stem Cells", Journal of Biomedicine and Biotechnology, vol. 2011, 12 pages, 2011.

*Primary Examiner* — Marcia S Noble
(74) *Attorney, Agent, or Firm* — Nixon Peabody LLP; Ronald Eisenstein; Candace Summerford

(57) ABSTRACT

Embodied herein are methods of reprogramming somatic cells or tissue stem cells to a more multipotent state or even a pluripotent state, the methods do not involve gene transfer of master transcription factor genes/proteins. The methods are also useful for rapid and efficient cloning of induced pluripotent stem cells after gene transfer of master transcription factor genes/proteins.

9 Claims, 11 Drawing Sheets

FIG. 3A
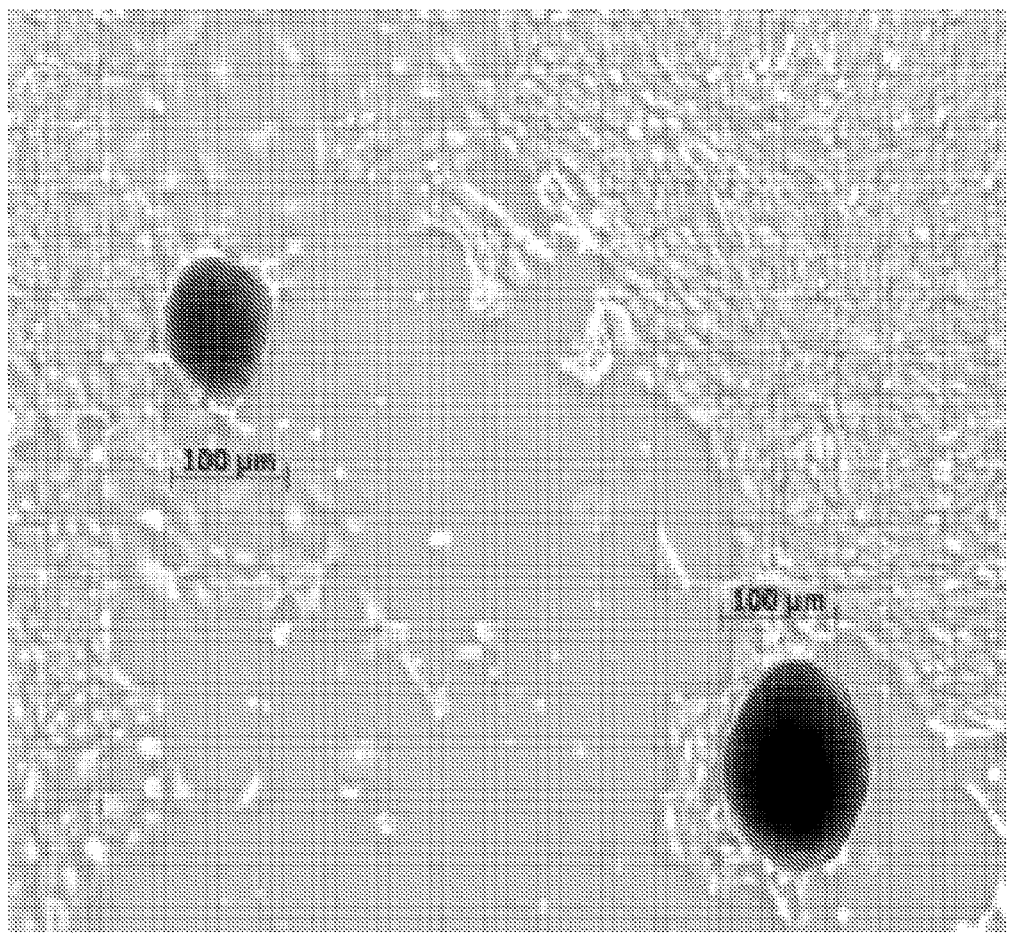
Phase    DAPI
  With Xn
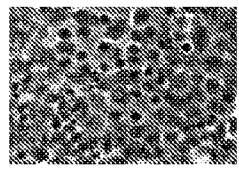 Without Xn
FIG. 3B

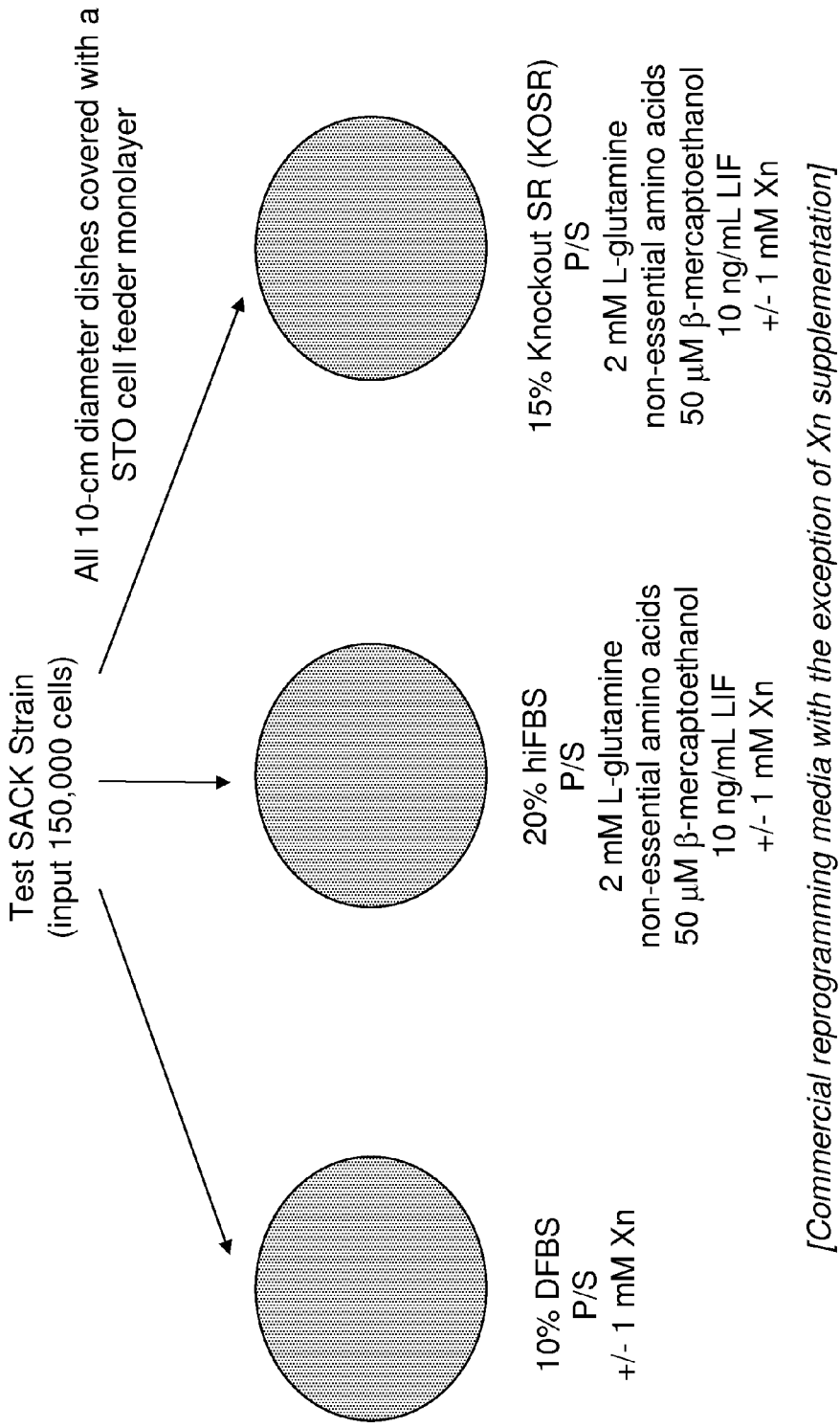

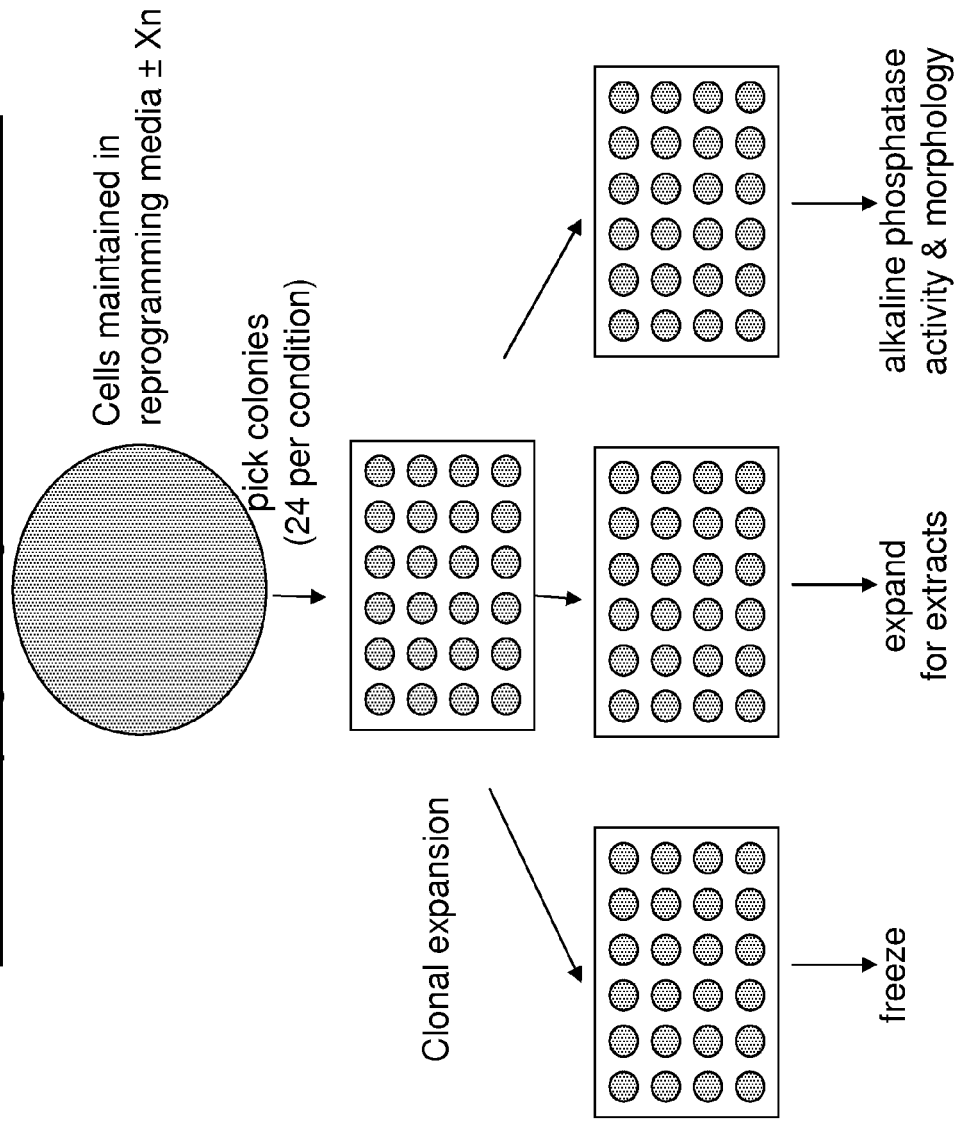

(No alkaline phosphatase (AP) activity detected)

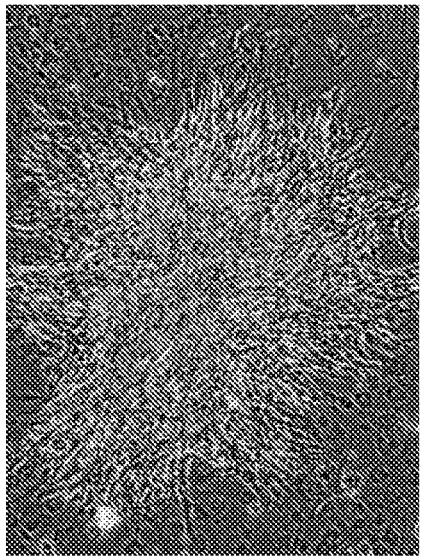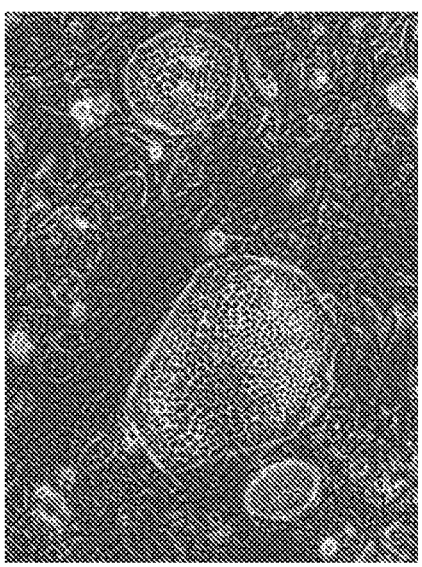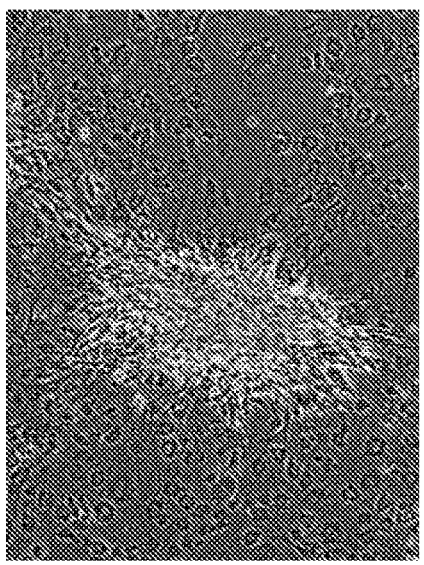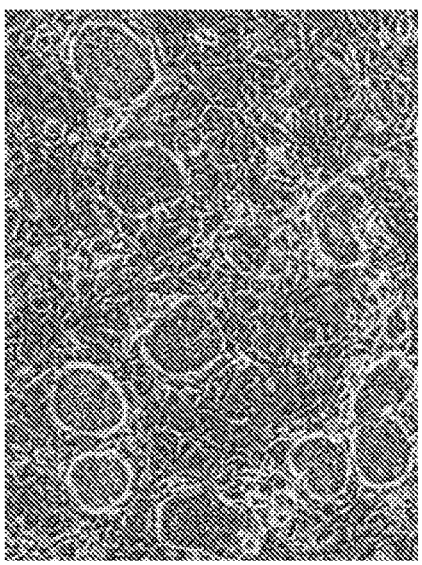
FIG. 7A
FIG. 7B

Panstra-25 Clone #85
(Medium = KOSR + Xn)
ES, AP+

Panstra-12 Clone #95
(Medium = KOSR + Xn)

ES, AP+

Panstra-12 Clone #89
(Medium = KOSR + Xn)

ES, AP+

Panstra-12 Clone #49
(Medium = KOSR *control*)
FI, AP+

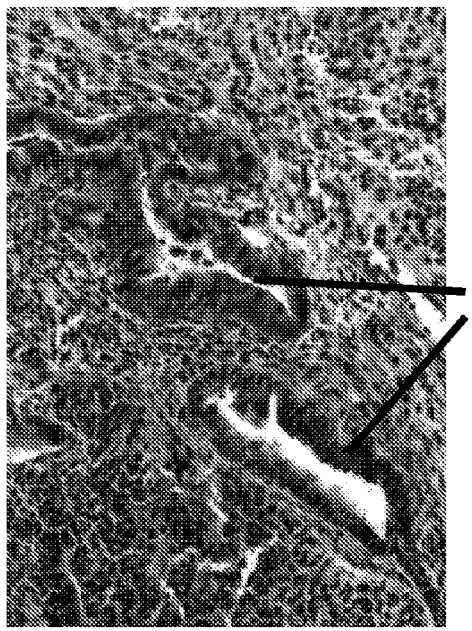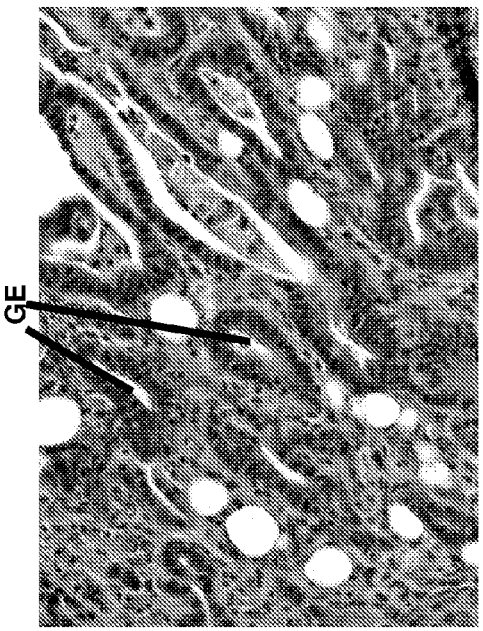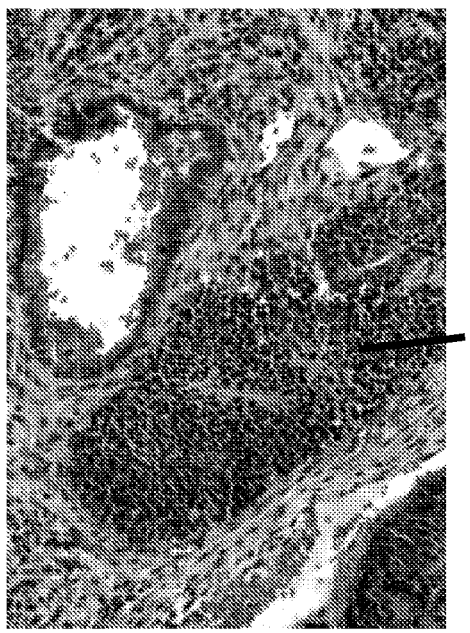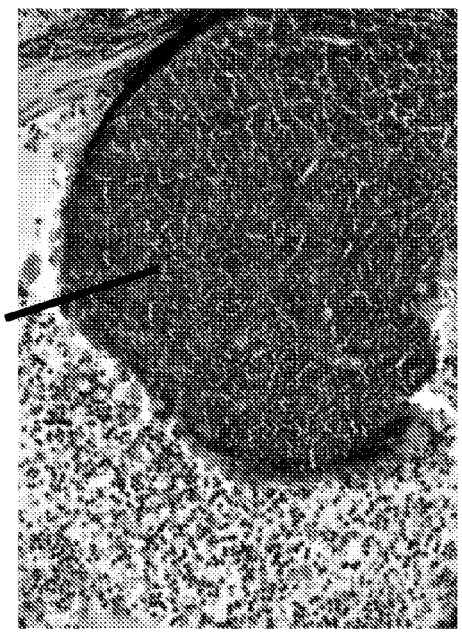
FIG. 11A ESC
FIG. 11B Panstra-12-KOSR-Xn-89

METHOD FOR CLONING PLURIPOTENT STEM CELLS

CROSS REFERENCE TO RELATED APPLICATIONS

This application is a 35 U.S.C. §371 National Phase Entry Application of International Application No. PCT/US2010/058939, filed Dec. 3, 2010, which designates the United States, and which claims benefit under 35 U.S.C. §119(e) of the U.S. provisional application No. 61/266,602 filed Dec. 4, 2009, the contents of which are incorporated herein by reference in their entireties.

GOVERNMENT SUPPORT

This invention was made with Government support under contract No. 5DP1OD000805 awarded by the National Institutes of Health, National Institute of General Medical Sciences. The Government has certain rights in the invention.

BACKGROUND OF INVENTION

Reprogramming of differentiated somatic cells to have a more undifferentiated stem cell-like state allow scientists to produce induced pluripotent stem cells (iPSCs). IPSCs derived from differentiated somatic cells of patients are potentially a powerful tool for biomedical research and may provide a source of cells for replacement therapies. However, the efficiency of producing and cloning such cells is low and the process can take more than four weeks. Human cell-based IPSC technology also does not present the ethical concerns of human embryonic stem cell technology, which is the only other technology that produces pluripotent stem cells.

Current methods of reprogramming of differentiated somatic cells involve increasing the amount of specific master transcription factors such as KLF4, OCT3/4, c-MYC, NANOG, LIN28, and SOX2 in the somatic cell. These master transcription factors are typically found in undifferentiated cells. They control the expression of other genes, many of which are themselves transcription factors that function to maintain a cell in the undifferentiated state. Currently, there are two main methods of increasing the amount of these master transcription factors: (1) by introducing exogenous genes of the master transcription factors using retroviruses, lentiviruses, or transfection of non-viral plasmids into the somatic cell thereby increasing the cellular expression; and (2) by introducing exogenous proteins of the master transcription factors into the somatic cell through certain transport channels of the cell. A minimum of three master transcription factors is required for reprogramming a differentiated somatic cell to a undifferentiated stem cell-like state, for example, by introducing OCT3/4 and SOX2 with either KLF4 and c-MYC or NANOG and LIN28. Therefore, to reprogram a somatic cell, at least several different exogenous genes or proteins need to be introduced into the cell.

One factor in determining the efficiency of obtaining a reprogrammed somatic cell is the success of introducing the exogenous genes or proteins into the somatic cell and the time that is required to isolate such a reprogrammed cell. Transformation efficiency of a single plasmid into a cell can be as low as less than one transformant cell for every 10,000 cells. The transformation efficiency for at least three independent plasmids representing three master transcription factors can be as low as one in $10^{12}$ cells. The use of virus-mediated transfection has improved the transduction efficiency somewhat. The average success rate of producing iPSCs by the virus-mediate method is roughly one in 10,000 cells and takes about four weeks from start to finish.

In addition, there are several problems associated with the current methods: for example, introduction of viral genes and gene products, integration of the exogenous genes or viral genes into the somatic cell genome and non-uniform transfection and/or expression of the exogenous genes and proteins. Therefore, methods that improve the rate and efficiency of producing reprogrammed somatic cells, preferably without transfection of exogenous genes or proteins, are desired, as they are crucial for enabling evaluations of the biomedical value of iPSCs.

SUMMARY OF THE INVENTION

Embodiments of the present invention are based on the discovery that adult stem cells expanded in culture by the method of suppression of asymmetric cell kinetics ("SACK;" e.g. See U.S. Pat. Nos. 7,645,610; 7,824,912, and 7,655,465) can be reprogrammed to undifferentiated (less differentiated) cells by culture in a cell growth media used for culturing embryonic stem cells (ESCs) in the absence of exogenous genes or proteins of the master transcription factors used for the production of iPSCs, i.e., Klf4, Oct3/4, c-Myc, Nanog, Lin 28, and Sox 2. In addition, embodiments of the invention are based on the discovery that addition of xanthine (Xn; the agent originally used to expand the adult stem cells by suppression of asymmetric cell kinetics) to culturemedia developed for the culture of pluripotent cells increased the efficiency and speed of production of iPSCs.

Accordingly, embodiments of the invention provide a method of reprogramming a tissue-specific adult stem cell (i.e., tissue stem cell) comprising contacting a tissue stem cell with Xn in a medium capable of supporting pluripotent stem cells, wherein the tissue stem cell is responsive to Xn or other SACK agent that has the ability to expand cellular guanine ribonucleotide pools, including, but not limited to, xanthosine and hypoxanthine. In the absence of Xn, a Xn-responsive tissue stem cell exhibits increased asymmetric self-renewal, which prevents its expansion; but in the presence of Xn, it exhibits increased symmetric self-renewal, which promotes its exponential expansion. As a guanine ribonucleotide precursor, Xn taken up from the medium expands guanine ribonucleotide pools, which causes a shift from asymmetric self-renewal to symmetric self-renewal by tissue stem cells. After 2 weeks of culture in pluripotent stem cell culture medium, Xn-responsive expanded tissue stem cells become reprogrammed without any additional treatment with an efficiency comparable to methods that employ gene or protein transfer.

In one embodiment, provided herein is a method of reprogramming a population of tissue stem cells comprising the steps of (a) contacting a population of cells comprising tissue stem cells with xanthine (Xn) in a culture medium; (b) culturing the population of cells comprising tissue stem cells of step (b) in the culture medium containing Xn for a sufficient amount of time to expand the tissue stem cells; and (c) culturing the population of cells comprising tissue stem cells from step (b) in a medium capable of supporting the maintenance of pluripotent cells or reprogrammed cells, wherein the medium is different from the culture medium used in step (a) and (b). In one embodiment, the population of tissue stem cells of step (b) undergoes suppression of asymmetric cell kinetics in the presence of Xn, thereby increasing the proportion of stem cells in the population of cells. In one embodiment, the tissue stem cell is a Xn-responsive cell.

In one embodiment, Xn is included in the medium capable of supporting the maintenance of pluripotent cells or reprogrammed cells. The inclusion of Xn into the medium capable of supporting the maintenance of pluripotent cells or reprogrammed cells functions to increase the efficiency of obtaining reprogrammed pluripotent cells.

In one embodiment, provided herein is a method of reprogramming a tissue stem cell comprising the steps of (a) clonally isolating a tissue stem cell from a population of cells in a culture medium comprising xanthine (Xn); and (b) culturing the isolated tissue stem cell in a medium capable of supporting the maintenance of pluripotent cells or reprogrammed cells.

In one embodiment, the tissue stem cell is clonally isolated by suppression of asymmetric kinetics in the presence of Xn. The inclusion of Xn into the medium capable of supporting the maintenance of pluripotent cells or reprogrammed cells functions to increase the efficiency of obtaining reprogrammed pluripotent cells.

In one embodiment, the medium capable of supporting the maintenance of pluripotent cells or reprogrammed cells comprised Xn.

Another embodiment of the present invention is a method for increasing the efficiency of reprogramming somatic cells or tissue stem cells comprising contacting the cell to be reprogrammed with a medium capable of supporting reprogramming of somatic cells wherein the medium comprises Xn.

In one embodiment, the concentration of xanthine is about 1 mM. Other purine nucleotide precursors such as xanthosine and hypoxanthine can also be used. Ideally, the concentrations should be about between 0.5-10 mM.

In one embodiment, the somatic cell or tissue stem cell is reprogrammed to a pluripotent state. In one embodiment, the reprogrammed somatic cell or tissue stem cell has embryonic stem cell-like characteristics, such as high expression of master transcription factor genes associated with embryonic stem cell, e.g., Klf4, Myc and Oct3/4. In one embodiment, the reprogrammed somatic cell or tissue stem cell is transduced with exogenous genes of the master transcription factor genes associated with embryonic stem cell, e.g., Klf4, Myc and Oct314.

In one embodiment, the tissue stem cell is selected from the group of liver stem cells, hair follicle stem cell, and pancreas stem cell.

Another embodiment of the present invention is a method of reprogramming a tissue stem cell comprising the steps of: (a) clonally isolating a tissue stem cell from a population of cells; and (b) contacting a tissue stem cell with xanthine (Xn) in a medium capable of supporting the reprogramming of cells.

In one embodiment, the tissue stem cell is isolated by suppression of asymmetric kinetics using Xn.

BRIEF DESCRIPTION OF THE DRAWINGS

FIG. 3A shows the pancreatic differentiation of SACK-R strain Panstra-25 wherein formation of islet-like clusters occurred after induction of differentiation in Xn-free medium, which promotes asymmetric self-renewal with production of tissue-specific differentiated cells.

FIG. 3B shows cells three days after the induction of differentiation. Upper panels, routine culture conditions with Xn supplementation; lower panels, Xn-free differentiation conditions. DAPI, detection of corresponding cell nuclei. The expression of insulin was detected by immunofluorescence (data not shown).

FIG. 4 shows the general schematics for gene-free reprogramming trials. Each tested SACK-derived cell strain was cultured on STO cell feeder monolayers in control medium with 10% DFBS, dialyzed fetal bovine serum (DFBS) or either of two commercial media for culture of murine embryonic stem cells (ESCs) and for the culture of reprogrammed cells such as iPSCs. Each medium condition was evaluated with or without supplementation with 1 mM xanthine (Xn). P/S denotes routine use of the antibiotics penicillin and streptomycin.

FIG. 5 shows the general schematics for clonal expansion of iPSC-like cells produced under gene-free reprogramming conditions from SACK-responsive cell strains.

FIGS. 7A and 7B show the cell colony morphology of SACK-responsive Panstra-25 cells under gene-free reprogramming conditions. These cells adopt two distinct colony morphologies, a fibroblast-like morphology and an ESC-like/iPSC-like morphology.

FIG. 7A shows fibroblastic cell colonies of Panstra-25 cells under gene-free reprogramming conditions.

FIG. 7B shows mouse embryonic stem cell-like (ESC-like) colonies of Panstra-25 cells under gene-free reprogramming conditions, indicative of the pluripotent phenotype.

FIG. 11A shows the hematoxylin-eosin stained tissue sections from a tumor originating from mouse ESCs. tumors. C: cartilage (mesoderm); GE: glandular epithelium (endoderm). produced by medium-only reprogrammed SACK-derived mouse pancreatic adult stem cells.

FIG. 11B shows the hematoxylin-eosin stained tissue sections from a tumor produced by medium-only reprogrammed SACK-derived mouse pancreatic adult stem cells, clone Panstra-12-KOSR-Xn-89. C: cartilage (mesoderm); GE: glandular epithelium (endoderm). produced by medium-only reprogrammed SACK-derived mouse pancreatic adult stem cells.

BRIEF LISTING OF THE TABLES

Figure 1:
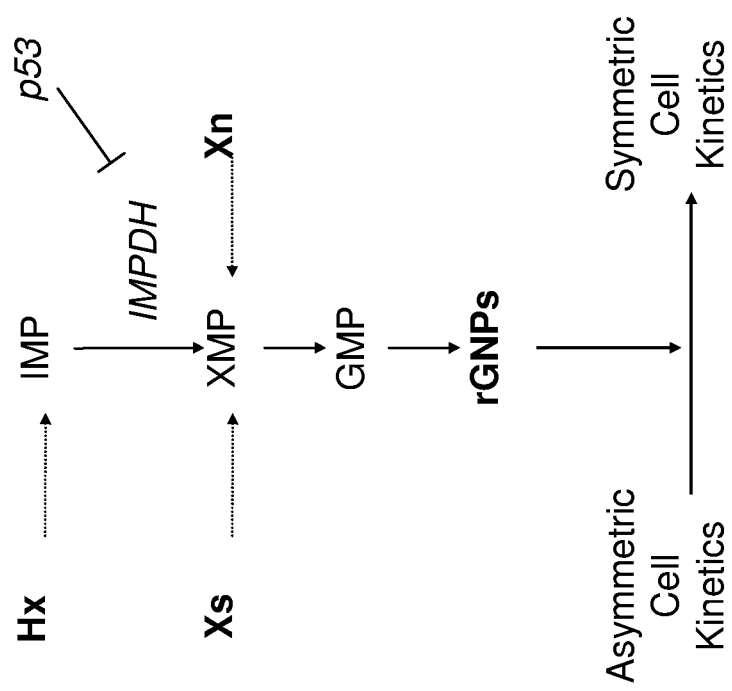
FIG. 1 shows the biosynthetic pathway underpinning the SACK principle. Three purine nucleoside precursors, hypoxanthine (Hx), xanthosine (Xs), and xanthine (Xn) have SACK activity by virtue of overcoming the negative regulation of p53 on guanine ribonucleotide (rGNP) biosynthesis, which is effected by down-regulation of inosine monophosphate dehydrogenase (IMPDH), the rate limiting enzyme in the pathway, by the action of p53.

Table 1. Tissue distribution of transplanted SACK-derived pancreatic cell strains in mice as detected by PCR.

Table 2. Micro-array expression levels for described iPSC reprogramming gene mRNAs in SACK-derived mouse pancreatic stem cell strains. Panstra-25 is a strain that shows a high degree for SACK-responsiveness. Panstra-11 is a non-responsive strain.

Table 3. Gene-free iPSC reprogramming properties of SACK-responsive (R) and non-responsive (NR) cell strains. A SACK-R strain is by definition a tissue stem cell strain. Pdx1 is a marker of early embryonic pancreatic development.

Table 4. Summary of the expansion efficiency of different colony types produced from SACK-responsive, Pdx1-positive Panstra-25 pancreatic stem cells under control (DFBS) and gene-free reprogramming conditions.

Table 5. Summary of the induction efficiencies of different colony types produced from SACK-responsive, Pdx1-positive Panstra-25 pancreatic stem cells under control (DFBS) and gene-free reprogramming conditions.

Table 6. Summary of the expansion efficiency of different colony types produced from SACK-responsive, Pdx1-negative Panstra-12 pancreatic stem cells under control (DFBS) and gene-free reprogramming conditions.

Table 7. Summary of the induction efficiencies of different colony types produced from SACK-responsive, Pdx1-negative Panstra-12 pancreatic stem cells under control (DFBS) and gene-free reprogramming conditions.

DETAILED DESCRIPTION OF THE INVENTION

Embodiments of the present invention are based on the discovery that mouse, SACK-expanded, Xn-responsive pancreatic tissue stem cells can be reprogrammed to an undifferentiated pluripotent state by only culturing in medium used to support the growth of mouse embryonic stem cells, in the absence of exogenous genes or proteins of the master transcription factors used for the production of iPSCs, e.g., Klf4, Oct3/4, c-Myc, Nanog, Lin 28, and Sox 2. In addition, embodiments of the invention are based on the discovery that addition of Xn to the reprogramming media increased the efficiency and rate of pluripotent reprogramming.

Accordingly, embodiments of the invention provide a method of reprogramming a tissue stem cell comprising contacting a tissue stem cell with Xn in a media capable of supporting the growth of pluripotent cells, wherein the tissue stem cell is responsive to xanthine. In the absence of Xn, a tissue stem cell responsive to Xn exhibits asymmetric self-renewal, which prevents its expansion and fosters the production of tissue-specific differentiated progeny cells; whereas culture in the presence of Xn causes a shift to symmetric self-renewal, which promotes exponential expansion of tissue stem cells, without production of differentiated progeny cells. Xn is a guanine ribonucleotide precursor. Its uptake promotes expansion of cellular guanine ribonucleotide pools, which promotes the shift from asymmetric self-renewal to symmetric self-renewal by tissue stem cells. After 2 weeks of culture in media that support the growth of pluripotent cells, Xn-responsive tissue stem cells reprogram to a pluripotent state without exogenous reprogramming transcription factors.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "growth factor" refers to a protein, peptide or other molecule having a proliferative, viability, division arrest, or differentiation effect on any cell type present in the cell system under consideration. Growth factors that can be used include any trophic factor that promotes stem cells to proliferate, including any molecule that binds to a receptor on the surface of the cell to exert a proliferative effect on the cell. Preferred proliferation-inducing growth factors include EGF, amphiregulin, acidic fibroblast growth factor (aFGF or FGF-1), basic fibroblast growth factor (bFGF or FGF-2), transforming growth factor alpha (TGFalpha.), and combinations thereof. Growth factors are usually added to the culture medium at concentrations ranging between about 1 ng/ml to 1 microg/ml. Concentrations about between 1 to 100 ng/ml are usually sufficient. Titration experiments can be performed to determine the optimal concentration of a particular growth factor.

In addition to proliferation-inducing growth factors, other growth factors can be added to the culture medium that influence viability and differentiation of the cells including NGF, platelet-derived growth factor (PDGF), thyrotropin releasing hormone (TRH), transforming growth factor betas (TGFβ), insulin-like growth factor (IGF-1) and the like.

The term "isolated" as used herein signifies that the cells are placed into conditions other than their natural environment. The term "isolated" does not preclude the later use of these cells thereafter in combinations or mixtures with other cells.

As used herein, the term "expanding" refers to increasing the number of like cells through symmetrical cell division (mitosis). The term "proliferating" and "expanding" are used interchangeably.

The term "reprogramming" as used herein refers to a process that reverts a cell from a late developmental stage of phenotypic restriction (i.e., differentiated) to an earlier developmental stage of phenotypic potential (i.e., undifferentiated)

at which a greater number of phenotypic lineages are available to progeny cells. In one embodiment, when complete, reprogramming yields iPSCs that have the ability to produce progeny cells inclusive of the full range of possible developmental phenotypes. In another embodiment, the reprogramming may be incomplete or partial, yielding less differentiated cells that can recapitulate only a subset of the full range of developmental phenotypes, but still many more than were available before the reprogramming. In one embodiment, reprogramming refers to a process of driving the differentiation of a cell backwards to a more undifferentiated or more primitive type of cells. In some embodiment, reprogramming encompasses reversion of differentiation state of a differentiated cell, (e.g., a stomatic stem cell) no a pluripotent state.

In some embodiments, reprogramming of a differentiated cell (e.g., a somatic cell or tissue stem cell) causes the differentiated cell to assume a pluripotent-like state. The resulting cells are referred to herein as "reprogrammed cells" or "undifferentiated cells".

Reprogramming involves alteration, e.g., reversal, of at least some of the heritable patterns of nucleic acid modification (e.g., methylation), chromatin condensation, epigenetic changes, and genomic imprinting, etc., that occur during cellular differentiation as a zygote develops into an adult, the result being a change from a differentiated to an undifferentiated state. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions used in methods of the invention (e.g. xanthine) may also be of use for such purposes. The methods of the present invention contribute to establishing the pluripotent state. The methods can be practiced on cells that are fully differentiated and/or restricted to giving rise only to cells of that particular type, rather than on cells that are already multipotent or pluripotent.

The term "reprogrammed cell" as used herein refers to a cell which has been reprogrammed from a differentiated cell according to the methods as disclosed herein, for example reprogrammed to a pluripotent state, a multipotent state, or a more undifferentiated state than the originally treated cell. The term "reprogrammed cell" encompasses an undifferentiated cell compared to the stage of differentiation of the starting treated cell.

In one embodiment, the reprogrammed cell has not been completely reprogrammed to a pluripotent state but rather to a non-pluripotent stable intermediate state, e.g., a cell that can differentiate into one or two of three germ layers, but cannot differentiate into all three of the germ layers. In some embodiments, the reprogrammed cell expresses at least one or at least two or at least three but not all of the following markers; alkaline phosphatase (AP), NANOG, OCT-4, SOX-2, SSEA4, TRA-1-60 or TRA-1-81. In some embodiments, the reprogrammed cell expresses markers from one or two germ cell layers, but not markers from all three embryonic germ layers (i.e. a partially reprogrammed cell does not express markers from all three layers of endoderm, mesoderm or ectoderm layers). Markers of endoderm cells include, Gata4, FoxA2, PDX1, Nodal, Sox7 and Sox17. Markers of mesoderm cells include, Brachycury, GSC, LEF1, Mox1 and Tie1. Markers of ectoderm cells include criptol, EN[1], GFAP, Islet 1, LIM1 and Nestin. In some embodiments, the reprogrammed cell is an undifferentiated cell.

The term "contacting" or "contact" as used herein as in connection with contacting a differentiated cell (e.g. tissue stem cell) with a compound as disclosed herein (e.g. xanthine, hypoxanthine, xanthosine, or another compound having a xanthine nucleus), includes subjecting the cell to a culture media, which comprises the compound. Where the differentiated cell is in vivo, contacting the differentiated cell with a compound includes administering the compound in a composition to a subject via an appropriate administration route such that the compound contacts the differentiated cell in vivo.

The term "pluripotent" when used in reference to a "pluripotent cell" refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, using, for example, a nude mouse teratoma formation assay. Pluripotency is also evidenced by the expression of embryonic stem (ES) cell markers, although a preferred test for pluripotency is the demonstration of the capacity to differentiate into cells of each of the three germ layers. In some embodiments, a pluripotent cell is an undifferentiated cell.

The term "pluripotency" or a "pluripotent state" as used herein refers to a pluripotent cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "multipotent" when used in reference to a "multipotent cell" refers to a cell that is able to differentiate into some but not all of the cells derived from all three germ layers; or multiple cell types that constitute a single type of tissue or organ. Thus, a multipotent cell is a partially differentiated cell. Multipotent cells are well known in the art, and examples of multipotent cells include tissue stem cells, such as for example, hematopoietic stem cells and neural stem cells, hair follicle stem cells, liver stem cells etc. Multipotent means a stem cell can form many types of cells in a given lineage, but not cells of other lineages. For example, a multipotent blood stem cell can form the many different types of blood cells (red, white, platelets, etc. . . . ), but it cannot form neurons; cardiovascular progenitor cell (MICP) differentiate into specific mature cardiac, pacemaker, smooth muscle, and endothelial cell types; pancreas-derived multipotent progenitor (PMP) colonies produce cell types of pancreatic lineage (cells that produces insulin, glucagon, amylase or somatostatin) and neural lineage (cells that are morphologically neuron-like, astrocytes-like or oligodendrocyte-like).

The term "multipotency" refers to a cell with the degree of developmental potential that is less than totipotent and pluripotent.

The term "totipotency" refers to a cell with the developmental capacity to yield all of the cells in the adult body as well as the extra-embryonic tissues including the placenta. The fertilized egg (zygote) is totipotent as are the early cleaved cells (blastomeres)

As an absolute, the term "differentiated cell" means any cell that does not have stem cell capacity, where stem cell capacity is the ability to divide in a manner that renews a baseline state of relative undifferentiation (stem cell phenotype) will simultaneously producing cells of different and developmentally more restricted state of differentiation (i.e. differentiated non-stem cells). In practice, the terms differentiated and undifferentiated always require a developmental reference, whether explicit or implicit. Tissue stem cells are undifferentiated relative to their differentiated, non-stem progeny cells. However, relative to iPSCs, embryonic stem cells, and embryonic precursor cells, tissue stem cells are more differentiated. It should be noted that placing many primary cells in culture can lead to some loss of fully differentiated characteristics. Thus, simply culturing such cells are included in the term differentiated cells and do not render these cells tissue stem cells or pluripotent cells. The transition of a differentiated cell to pluripotency requires a reprogramming stimulus beyond the factors that lead to partial loss of differentiated character in culture. Reprogrammed cells also have the characteristic of the capacity of extended passaging without loss of proliferative potential, relative to their primary cell parents, which generally have capacity for only a limited number of divisions in culture.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germ line cells. In mammals, germ line cells (also known as "gametes") are the spermatozoa and ova, which fuse during fertilization to produce a cell called a zygote, from which the entire mammalian embryo develops. Every other cell type in the mammalian body—apart from the sperm and ova,—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments, the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell can be performed both in vivo and in vitro (where in vivo is practiced when a differentiated cell is present within a subject, and where in vitro is practiced using isolated differentiated cell maintained in culture). In some embodiments, where a differentiated cell or population of differentiated cells are cultured in vitro, the differentiated cell can be cultured in an organotypic slice culture, such as described in, e.g., Meneghel-Rozzo et al., 2004, Cell Tissue Res, 316:295-303, which is incorporated herein in its entirety by reference.

As used herein, the term "adult cell" refers to a cell found throughout the body after embryonic development.

As used herein, the terms "iPS cell" and "induced pluripotent stem cell" are used interchangeably and refers to a pluripotent cell technically derived (e.g., induced by complete or partial reversal) from a differentiated cell (e.g. a non-pluripotent cell), typically an adult differentiated cell, for example, by contacting the cell with at least one compound of any compounds selected from xanthine, xanthosine, hypoxanthine, or analogs thereof, e.g. compounds with a xanthine nucleus.

The term "progenitor cell" is used herein to refer to cells that have a cellular phenotype that is at an earlier step along a developmental pathway or progression than is a later differentiated cell relative to a cell to which it can give rise by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. Progenitor cells are distinct from tissue stem cells in that they lack asymmetric self-renewal. In the absence of their own producer stem cell, progenitor cells' populations are rapidly exhausted because of their inability to simultaneously preserve their own initial degree of differentiation.

The term "tissue stem cell" as used herein, refers to a tissue cell that has the ability to undergo repeated divisions that yield both cells that are phenotypically identical to itself and cells that are phenotypically distinct, i.e., are differentiated with respect to the stem cell parent. This dichotomy of function may be accomplished by determined asymmetric self-renewal in which each stem cell division produces both types of cells; or by population-based asymmetric self-renewal in which small populations of tissue stem cells divide and randomly produce both types of cells at frequencies that are sufficient to maintain the stem cell fraction indefinitely. In one embodiment the differentiating cell immediately differentiates. In another embodiment, the differentiating cell is a progenitor cell that divides to produce more differentiated tissue cells that execute the developmental plan of the tissue. Cellular differentiation is a complex process typically occurring through many cell divisions. A differentiated cell may derive from a multipotent cell which itself is derived from a multipotent cell, and so on. While each of these multipotent cells can be tissue stem cells in their own right, the range of cell types each can give rise to may vary considerably. In many biological instances, stem cells are "multipotent" because they can produce progeny of more than one distinct cell type, but this is not required for "stem-ness." Tissue stem cells can be unipotent as well, producing on one type of differentiated progeny cell.

In the context of cell ontogeny, the term "differentiate", or "differentiating" is a relative term meaning a "differentiated cell" is a cell that has progressed further down the developmental pathway than its precursor cell. Thus, in some embodiments, a reprogrammed cell as this term is defined herein, can differentiate to lineage-restricted precursor cells (such as a mesodermal stem cell or a endodermal stem cell), which in turn can differentiate into other types of precursor cells further down the pathway (such as a tissue specific precursor, for example, a cardiomyocyte precursor, or a pancreatic precursor), and then to an end-stage differentiated cell, which plays a characteristic role in a certain tissue type, and may or may not retain the capacity to proliferate further.

The term "tissue stem cell" is used to refer to any multipotent or unipotent stem cell derived from non-embryonic tissue, including fetal, juvenile, and adult tissue. Tissue stem cells have been isolated from a wide variety of adult tissues including blood, bone marrow, brain, olfactory epithelium, skin, pancreas, skeletal muscle, and cardiac muscle. Each of these tissue stem cells can be characterized based on gene expression, factor responsiveness, and morphology in culture. Exemplary tissue stem cells include liver stem cells, hair follicle stem cells, neural stem cells, neural crest stem cells, mesenchymal stem cells, hematopoietic stem cells, and pancreatic stem cells. As indicated above, tissue stem cells have been found resident in virtually every tissue. "Adult stem cell," "somatic stem cell" and "tissue stem cell" are used interchangeably.

The term a "reprogramming gene", as used herein, refers to a gene whose expression, contributes to the reprogramming of a differentiated cell, e.g., a mature differentiated cell to an undifferentiated cell that maintains a pluripotent state or partially pluripotent state. A reprogramming gene can be, for example, genes encoding master transcription factors Sox2, Oct3/4, Klf4, Nanog, Lin-38, c-myc and the like.

The term "exogenous" refers to a substance present in a cell that was introduced from outside the cell by either a natural process or a biotechnology. The terms "exogenous" when used herein refers to a nucleic acid (e.g., a nucleic acid encoding a reprogramming transcription factor, e.g., SOX2, OCT3/4, KLF4, NANOG, LIN-38, c-MYC and the like) or a protein (e.g., a transcription factor polypeptide) that has been introduced by a process involving the hand of man into a biological system such as a cell or organism in which it is not normally found or in which it is found in lower amounts. A substance (e.g. a nucleic acid encoding a SOX2 transcription factor, or a protein, e.g., a SOX2 polypeptide) will be considered exogenous if it is introduced into a cell or an ancestor of the cell that inherits the substance. In contrast, the term "endogenous" refers to a substance that is produced within the cell by natural processes.

The terms "SACK-R" and "Xn-responsive" when used in reference to a cell characteristic means the cell exhibits asymmetric self-renewal in the absence of Xn, but symmetric self-renewal in Xn supplemented medium. At the population level, SACK-R cell cultures exhibit a faster overall rate of cell proliferation when the culture medium is supplemented with Xn. The terms "SACK-R" and "Xn-responsive" are used interchangeably. Xn-responsive cells are not transformed cells.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The terms "enriching" or "enriched" are used interchangeably herein and mean that the yield (fraction) of cells of one type is increased by at least 10% over the fraction of cells of that type in the starting culture or preparation.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

In one embodiment, the invention provides a method of reprogramming a tissue stem cell that is performed in vitro, i.e., the tissue stem cell is isolated and maintained in culture. In another embodiment, the invention provides a method of reprogramming a tissue stem cell that is performed in vivo, i.e., when the somatic cell is present within a subject. In one embodiment, the subject is a mammal, such as human, pig, goat, sheep and mouse. In some particular embodiments, the mammal is a primate mammal such as humans and monkeys.

In one embodiment, the invention provides a method of reprogramming a tissue stem cell comprising selecting for a tissue stem cell and contacting the tissue stem cell with Xn in a media capable of supporting pluripotent cells, wherein the tissue stem cell is responsive to xanthine. In addition to exhibiting asymmetric self-renewal in the absence of Xn, the Xn-responsive tissue stem cells can uptake Xn from the medium wherein Xn serves as a guanine ribonucleotide precursor.

Tissue stem cells of the present invention include any stem cells isolated from fetal, neonatal, post-natal, or adult tissues. Tissue stem cells include but are not limited to bone marrow-derived stem cells, umbilical cord blood stem cells, amniotic stem cells, adipose-derived stem cells, mesenchymal stem cells, neural stem cells, liver stem cells, and pancreatic stem cells. Bone marrow-derived stem cells refer to all stem cells derived from bone marrow; these include but are not limited to mesenchymal stem cells, bone marrow stromal cells, and hematopoietic stem cells. Bone marrow stem cells are also known as mesenchymal stem cells or bone marrow stromal stem cells, or simply stromal cells or stem cells. These tissue stem cells can be isolated by any methods known the art, e.g., as taught in U.S. Pat. Nos. 6,878,542, 6,436,704, 6,927,061, 6,911,533, 7,052,907, 7,560,280, 7,592,174, U.S Patent Publication No. 20090238803, and WO/2003/016916. In one embodiment, the tissue stem cells are isolated from tissues.

Tissue stem cells exhibit asymmetric cell kinetics (also know as asymmetric self-renewal; Rambhatla et al., J. Biomed. Biotechnol. 2001; 1: 28-37; Sherley J L., Stem Cells. 2002, 20:561-72). Asymmetric cell kinetics can be suppressed by Xn and other guanine nucleotide precursors in order to proliferate and expand a population of tissue stem cells in vitro. Suppression of asymmetric kinetics by Xn to expand tissue stem cells (e.g., undifferentiated adult cells) in vitro gives rise to a population of undifferentiated tissue stem cells that are responsive to Xn and that are SACK-R. Accordingly, in one embodiment, the methods of the invention comprises enriching for a population of tissue stem cells by culturing a population of somatic cells, that comprises tissue stem cells, in the presence of Xn in order to expand the population of tissue stem cells (See for example, U.S. Pat. Nos. 7,645,610; 7,824,912, and 7,655,465, hereby incorporated by reference in their entirety). The expanded population of tissue stem cells (or optionally clonally isolated and expanded tissue stem cell) is then exposed to reprogramming media containing Xn, as described herein, in order to reprogram the expanded population of tissue stem cells, e.g., into induced pluripotent stem cells. In one embodiment, tissue stem cells are expanded, and optionally isolated (e.g., clonally isolated), by suppression of asymmetric cell kinetics using a guanine nucleotide precursor e.g., xanthine, xanthosine and hypoxanthine.

In one embodiment, the asymmetric cell kinetics is suppressed by Xn, thus the tissue stem cells are responsive to Xn and are SACK-R. In one embodiment, tissue stem cells are isolated by suppression of asymmetric cell kinetics using a guanine ribonucleotide precursor, e.g., xanthine, xanthosine and hypoxanthine Means for selection of tissue stem cells using a guanine ribonucleotide precursor are known to those skilled in the art, e.g., as described in Lee H S et al., Biotechnol. Bioeng. 2003, 83:760-71.

Tissue stem cells are adult stem cells that are multipotent or unipotent (e.g., sperm stem cells or lens stem cells). By reprogramming them, they become closer to an embryonic stem cell-like state, are less multipotent (or unipotent) and are more pluripotent. For example, a muscle satellite cell is the most developmentally differentiated form of skeletal muscle progenitor cell that will produce differentiated muscle cells under appropriate conditions, e.g., tissue injury or regeneration. According to the method of the invention, a muscle satellite cell can be reprogrammed to a pluripotent cell that then can be directed to produce a non-muscle cell such as a nerve cell or a skin cell. In one embodiment, a tissue stem cell reprogrammed to an embryonic stem cell-like cell that expresses alkaline phosphatase. In one embodiment, a tissue stem cell reprogrammed to an embryonic stem cell-like cell that expresses embryonic stem cell surface markers that are known in the art, e.g., SSEAs and TRAs. In another embodiment, a tissue stem cell is reprogrammed to an embryonic stem cell-like cell that is able to form teratomas and embryoid bodies (EBs). EBs consist of a disorganized array of differentiated or partially differentiated cell types that are derived from the three primary developmental germ layers of the embryo—the endoderm, mesoderm, and ectoderm. Teratomas that form in animals from embryonic stem cells that are composed of disorganized tissues derivative of all three germ layers, like EBs in vitro, are another manifestation of stem cell pluripotency.

In one embodiment of the method, no gene or protein transfer takes place in the tissue stem cell. Specifically, exogenous genes or proteins of master transcription factors (also known as reprogramming genes or proteins) that are known to induce pluripotent reprogramming, i.e., Klf4, Oct3/4, c-Myc, Sox-2 and Nanog, are not transfected or introduced into the tissue stem cells. The inventors have shown that when SACK-expanded tissue cells are cultured in Xn supplemented medium, there is increased Klf4 and c-Myc expression from the endogenous genes (see Table 2).

In one embodiment, the tissue stem cell is isolated in a culture medium supplemented with Xn through the suppression of asymmetric cell kinetics. The culture medium for isolation of tissue stem cells can be for a somatic cell or a tissue stem cell (e.g., in U.S. Patent Application Nos. 2005/0272147 and 2004/0018620; Lee H S, et al., Biotechnol. Bioeng. 2003, 83:760-71).

In one embodiment, the tissue stem cells uptake and metabolize Xn. A skilled artisan in the art can easily utilize standard biochemical analyses for assessing the uptake and metabolism of Xn. For example, standard biochemical analyses using radioactive Xn and HPLC with radiometric detection or heavy isotope Xn (e.g., N15-substituted) followed by mass spectrometry detection of Xn-derived metabolites. In either case, the labeled analogue is given to cells; and, at different times after addition, the cells are harvested, washed, and hydrolysed in perchloric acid. Neutralized perchlorate hydrolysates are then analyzed for intact labeled Xn and labeled Xn metabolites (e.g., XMP, GMP) and catabolites (e.g., uric acid) produced by cells.

In one embodiment, the invention provides a method of reprogramming a tissue stem cell comprising selecting and isolating for a tissue stem cell or a Xn-responsive cell (SACK-R) by contacting a population of cells with Xn in a culture medium and then contacting the isolated tissue stem cell with Xn in a media that support the culture maintenance of pluripotent cells or reprogrammed cells. In one embodiment, the culture medium is not one that can support the maintenance of pluripotent cells or reprogrammed cells, but one that supports regular cell maintenance and expansion of cells in culture. In addition to exhibiting asymmetric self-renewal in the absence of Xn, the Xn-responsive tissue stem cells can uptake Xn from the medium into the cell wherein Xn serves as a guanine ribonucleotide precursor and promotes symmetric self-renewal with exponential expansion of the tissue stem cells.

In one embodiment, the invention provides a method of reprogramming a population of tissue stem cells comprising the steps of (a) contacting a population of cells comprising tissue stem cells with xanthine (Xn) in a culture medium; (b) culturing the population of cells comprising tissue stem cells of step (a) in the culture medium containing Xn for a sufficient amount of time to expand the number of tissue stem cells; and (c) culturing the population of cells comprising tissue stem cells from step (b) in a medium capable of supporting the maintenance of pluripotent cells or reprogrammed cells, wherein the medium is different from that of the culture medium of step (a) and (b).

In some embodiments, the sufficient amount of time is at least 2, passages of cells, at least 5, at least 7, at least 10, at least 15, at least 20, at least 15, at least 30, at least 35, at least 40, or at least 50 passages of cells. Methods of cell culture passaging is well known in the art.

In one embodiment, the population of tissue stem cells of step (b) undergoes suppression of asymmetric cell kinetics in the presence of Xn, thereby increasing the proportion of stem cells in the population of cells. In other words, tissue stem cells are expanded in the presence of Xn. In one embodiment, tissue stem cell is a Xn-responsive cell.

In another embodiment, Xn is included in the medium capable of supporting the maintenance of pluripotent cells or reprogrammed cells.

In one embodiment, the invention provides a method of reprogramming a tissue stem cell comprising the steps of (a) clonally isolating a tissue stem cell from a population of cells in a culture medium comprising xanthine (Xn); and (b) culturing the isolated tissue stem cell in a medium capable of supporting the maintenance of pluripotent cells or reprogrammed cells.

In one embodiment, the tissue stem cell is isolated by suppression of asymmetric kinetics in the presence of Xn.

In one embodiment, the medium capable of supporting the maintenance of pluripotent cells or reprogrammed cells comprised Xn.

In one embodiment, the invention provides a method of reprogramming a population of tissue stem cells comprising enriching for a population of tissue stem cells, or a Xn-responsive cells (SACK-R), by contacting a population of somatic cells with Xn in a culture media, culturing and passaging the population of somatic cells in the presence of Xn to expand and enrich the population of tissue stem cells (somatic stem cells), and then contacting the enriched population of somatic stem cells with media capable of supporting reprogramming of cells, where the reprogramming media can optionally contain Xn. In addition to exhibiting a slower growth rate in the absence of Xn, the Xn-responsive somatic stem cells can uptake Xn from the medium environment into the cell wherein Xn serves as a guanine nucleotide precursor in the Xn-responsive somatic cells.

In one embodiment, the invention provides a method of reprogramming a tissue stem cell comprising culturing a population of cells in xanthine to suppress asymmetric kinetics and clonally isolating Xn-responsive SACK-R cells; then contacting the isolated Xn-responsive SACK-R cell with Xn in media capable of supporting the growth of pluripotent cells.

In one embodiment, the tissue stem cell is selected and isolated with a culture medium for expanding a tissue stem cell. Such media are well known to one skilled in the art, e.g., in U.S. Pat. Nos. 7,422,736; 7,556,801 7,645,610; 7,824,912, 7,655,465 and 7,601,534. In another embodiment, the tissue stem cell is selected and isolated with a culture medium specific for expanding and propagating a mammalian cell in culture. Such culture media are also well known to one skilled in the art, e.g., in U.S. Pat. Nos. 5,342,777, 6,900,056, and 7,258,998. A skilled artisan would be able to select the appropriate culture medium for the type of tissue stem cells used in the method. In one embodiment, a cell culture medium for expanding and propagating a cell in culture typical comprises a near-neutral pH buffered aqueous medium, salts, essential amino acids, vitamins, glucose and/or L-glutamine and growth factors. Other supplemental components include but are not limited to non-essential amino acids, L-glutamine, sodium pyruvate, penicillin, streptomycin, beta-2-mercaptoethanol (beta 2ME) and serum,e.g., fetal calf serum (FCS), fetal bovine serum (FBS), or serum substitutes such as KNOCKOUT™ serum replacement reagent by INVITROGEN™ (KSR).

In one embodiment, the population of cells is derived from a tissue. In one embodiment, a population of cells is derived from any tissue, for example skin, hair follicle, pancreas or liver. Such tissues are cut into small pieces, treated to dissociate single cells from the tissue; and the liberated, single cells are immediately grown in culture medium supplemented with Xn. Subsequently, the cells are plated and grown at lower density, maintaining Xn supplementation, such that the clusters of cells arising from single cells after 1-10 cell divisions are still visually distinguishable from each other. These initial cells are plated at low cell density, ≤300 cells/cm$^2$. At this low cell density, after 5-10 symmetric cell divisions, these cells and their progeny are still physically distinct cell colonies and can be picked without cross-contamination. Each cluster of cells arising from a single cell is picked and all are used to grow in individual plates or wells, either in the presence of Xn or in the absence of Xn to establish the cell clones' responsiveness to Xn. In the examples, FIGS. 3 and 6 demonstrate that before iPSC conversion, pancreatic tissue stem cells lack the embryonic stem cell colony morphology and are alkaline phosphatase-negative. Lee H S, et al., Biotechnol Bioeng. 2003, 83:760-71 describes how liver stem cells are isolated and expanded.

In one embodiment, the invention provides a method comprising adding Xn to media capable of supporting the growth of pluripotent cells and thereby increase the efficiency of cloning of pluripotent cells when the media is used for reprogramming. The tissue stem cell is cultured in the medium that is supplemented with Xn and becomes reprogrammed to a more pluripotent state during the process of exposure to Xn.

In one embodiment, the invention provides a method for increasing the efficiency of reprogramming somatic cells or tissue stem cells comprising contacting the cell to be reprogrammed with a medium capable of supporting pluripotency of cells that comprises Xn. The cell to be reprogrammed can be reprogrammed by the introduction of exogenous reprogramming genes or proteins.

In any embodiments of the methods, any compound having a xanthine nucleus, e.g. xanthine, xanthosine, hypoxanthine, can be used to supplement the culture media described herein.

In any embodiments of the methods, the concentration of compound having a xanthine nucleus, e.g. xanthine (Xn), xanthosine (Xs), hypoxanthine (Hx), is about between 0.5 mM to 10 mM, including all the intervening concentrations, e.g., 0.5-1 mM, 0.5-1.5 mM, 0.5-2 mM, 0.5-4 mM, 0.5-6 mM, 0.5-8 mM, 1-1.5 mM, 1-2 mM, 1-2.5 mM, 1-3 mM, 1-3.5 mM, 1-4 mM, 1-5 mM, 1-6 mM, 1-8 mM, 1-10 mM, 1.5-2 mM, 1.5-2.5 mM, 1.5-3 mM, 1.5-3.5 mM, 2-3 mM, 2-4 mM, 2-6 mM, 2-8 mM, 2-9 mM, and 2-10 mM.

In any embodiments of the methods, Xn is used at a concentration of about 1 mM concentration in the culture medium.

In any embodiments of the methods, Xn is used at a concentration of at least 1 mM concentration in the culture medium. In other embodiments, Xn is used at a concentration of at least 1.5 mM or at least 2 mM.

In some aspects, the somatic cell can be any cell type in the body, e.g., skin, fat, cord blood, blood, amniotic, liver, hair follicle cell etc.

In one embodiment, the somatic cell to be reprogrammed is transfected with the exogenous genes of master transcription factors known to induce pluripotent reprogramming, i.e., Klf4, Oct3/4, c-Myc, Sox-2, Lin-28 and Nanog. In one embodiment, the transfection is mediated by viruses such as a lentivirus or a retrovirus. Such methods are well known in the art, e.g., in PCT/JP2006/324881, Japanese patent No 0.2008-131577, Takahashi K, et al., 2007, Cell 131:861-72, and Takahashi, K. and Yamanaka, S., 2006, Cell, 126:663-676. These references are hereby incorporated by reference in their entirety. Additional protocols can be obtained from the World Wide Web site for the Center for iPS Cell Research and Application (CiRA), Institute for Integrated Cell-Material Sciences (iCeMS) at Kyoto University. In one embodiment, the somatic cell that is transfected with the exogenous genes of master transcription factors known to induced pluripotent reprogramming exhibits asymmetric cell kinetics, which is suppressed by Xn. In one embodiment, the transfected somatic cell is responsive to Xn and is SACK-R.

In one embodiment, the somatic cell to be reprogrammed is transfected with the exogenous transcription factors known to induced dedifferentiation, i.e., Klf4, Oct3/4, c-Myc, Sox-2, Lin-28 and Nanog. Sheng Ding et al. generated of iPSCs from somatic cells without any genetic alteration of the adult somatic cell. Instead, a repeated treatment of the cells with certain proteins (i.e., Klf4, Oct3/4, c-Myc, Sox-2, Lin-28 and Nanog) channeled into the cells via poly-arginine anchors was sufficient to induce pluripotency (Cell Stem Cell, 2009, 4:381-384). This reference is hereby incorporated by reference in its entirety. In one embodiment, the somatic cell that is transfected with the exogenous proteins of transcription factors known to induce pluripotent reprogramming exhibits asymmetric cell kinetics, which is suppressed by Xn. In one embodiment, the transfected somatic cell is responsive to Xn. Additional protocols can be obtained from the World Wide Web site for "collaslab" period "corn".

In another embodiment, the somatic cell is contacted with fibroblast growth factor 2 (FGF2) under low oxygen conditions. The expression of pluripotency inducing genes can also be increased by treating somatic cells with FGF2 under low oxygen conditions (Raymond L. Page et. al., 2009, Cloning and Stem Cells, 11:417-426). This reference is hereby incorporated by reference in its entirety. In one embodiment, the somatic cell contacted with FGF2 under low oxygen conditions exhibits asymmetric cell kinetics, which is suppressed by Xn. In one embodiment, the somatic cell contacted with FGF2 under low oxygen conditions is responsive to Xn.

In another embodiment, the somatic cell is contacted with chemicals, e.g., thiazovivin, ALK5 inhibitor SB43142, and MEK inhibitor PD0325901. Ding and colleagues have shown that these inhibitor of the TGFβ (transforming growth factor beta) and the MEK (mitogen-activated protein kinase) pathways, when used singly and in combination dramatically improve the efficiency of creating stem cells from human adult tissue (Tongxiang Lin, et al., 2009, Nature Methods, 6:805-808). This reference is hereby incorporated by reference in its entirety. In one embodiment, the somatic cell contacted with ALK5 inhibitor SB43142 and MEK inhibitor PD0325901 exhibits asymmetric cell kinetics, which is suppressed by Xn. In one embodiment, the somatic cell contacted with ALK5 inhibitor SB43142 and MEK inhibitor PD0325901 is responsive to Xn.

In another embodiment, the somatic cell is contacted with thiazovivin, SB43142 and PD0325901. In one embodiment, the somatic cell contacted with thiazovivin, ALK5 inhibitor SB43142 and MEK inhibitor PD0325901 exhibits asymmetric cell kinetics, which is suppressed by Xn. In one embodiment, the somatic cell contacted with thiazovivin, ALK5 inhibitor SB43142 and MEK inhibitor PD0325901 is responsive to Xn.

The following are the general steps in a current typical protocol for reprogramming somatic cells involving exogenous genes and generating induced pluripotent stem cells:
  Step 1: selection and primary expansion of somatic cells, e.g., neonatal or adult human epidermal keratinocytes, neonatal or adult human dermal fibroblasts in media;
  Step 2: Reprogramming of somatic cells with maximal efficiency using lentiviral mediated input of reprogramming transcription factor transgenes or the expression of same transcription factors;
  Step 3: Selection and expansion of the reprogrammed cell that has induced pluripotent stem cell-like characteristics;
  Step 4: Validation of pluripotency of the induced pluripotent stem cell, e.g with antibody for expressions of embryonic stem cell specific markers such as alkaline phosphatase; Sonic Hedgehog (Shh); stage-specific embryonic antigens such as SSEA3, SSEA1, SSEA4; Klf-4, c-Myc, Sox 2, Oct4/5 expression. Pou5f1/Oct4 is a known marker for the pluripotent state; AFP: endoderm lineage marker; ACTC1: mesoderm lineage marker; or SOX1: ectoderm lineage marker.

Phosphatases have commonly been used as enzyme markers for the undifferentiated state of cells, allowing researchers to identify undifferentiated cells in a cell culture, such as primordial germ cells among a population of cells, to distinguish subpopulations of bone marrow stromal cells, and to investigate in vitro dedifferentiation in carcinoma cell lines.

Other markers for identifying the undifferentiated state of a cell include, but are not limited to, the sonic hedgehog protein (Shh) and the stage-specific embryonic antigens (SSEAs). Shh is a secreted protein that controls cell fate and mitogenesis in both vertebrates and invertebrates. SSEAs are cell-surface molecules that exhibit lineage-restricted patterns of expression during development. SSEA1 provides a surface marker for mouse and human primordial germ cells and mouse embryonic stem cells. Primitive endoderm expresses the SSEA3 epitope and finally this epitope is also expressed in human erythrocytes (Shevinsky L H, et al. 1982, Cell, 30:697-705). Mesenchymal stem cell-like cells isolated from human amniotic fluid also express SSEA3 (Kim J, et al., 2007, Cell, Prolif., 40:75-90). Besides human, rabbit embryonic stem cells and chicken testicular cells also express SSEA3 (Jung J G, et al., 2007, Biol. Reprod., 76:173-82). Using series of purified glycolipids, a more refined epitope corresponding to a unique globo-series ganglioside was characterized. (Kannagi R, et al., 1983, EMBO J., 2:2355-61) This antibody provides an extremely useful tool for looking into differential expression of SSEAs in various embryonic cell populations. These references are hereby incorporated by reference in their entirety.

In some embodiments, the somatic cell that is to be reprogrammed is derived from any mammal, such as human, pig, goat, sheep and mouse. In some particular embodiments, the mammal is a primate mammal such as humans and monkeys.

Suppression of Asymmetric Cell Kinetics

Adult tissue stem cells predominantly divide by asymmetric cell kinetics. While tissue stem cells also undergo limited symmetric divisions (that produce two identical stem cells) in developing adult tissues, such symmetric kinetics is restricted to periods of tissue expansion and tissue repair. Inappropriate symmetric tissue stem cell divisions evoke mechanisms leading to apoptosis of duplicitous stem cells. Some stem cells may also lie dormant for long periods before initiating division in response to specific developmental cues, as in reproductive tissues like the breast. However, the predominant cell kinetics state of tissue stem cells is asymmetric.

During asymmetric cell kinetics, one daughter cell divides with the same kinetics as its stem cell parent, while the second daughter gives rise to a differentiating non-dividing cell lineage. The second daughter may differentiate immediately; or depending on the tissue, it may undergo a finite number of successive symmetric divisions to give rise to a larger pool of differentiating cells. The second daughter and its dividing progeny are called transit cells. Transit cell divisions ultimately result in mature, differentiated, terminally arrested cells. In tissues with high rates of cell turnover, the endpoint for differentiated terminal cells is programmed cell death by apoptosis.

Asymmetric cell kinetics evolved in vertebrates as a mechanism to insure tissue cell renewal while maintaining a limited set of tissue stem cells and constant adult body mass. Mutations that disrupt asymmetric cell kinetics are an absolute requirement for the formation of a clinically significant tumor mass. In many ways, asymmetric cell kinetics provides a critical protective mechanism against the emergence of neoplastic growths that are life threatening.

In culture, continued asymmetric cell kinetics of explanted tissue stem cells is a major obstacle to their expansion in vitro. Ongoing asymmetric cell kinetics results in dilution and loss of an initial relatively fixed number of tissue stem cells by the accumulation of much greater numbers of their terminally differentiating progeny. If a sample includes both exponentially expanding differentiated cells as well as tissue stem cells, the number of the exponentially expanding cells, though finite, will rapidly overwhelm the tissue stem cells, leading to their dilution.

One regulator of asymmetric cell kinetics is the p53 tumor suppressor protein. Several stable cultured murine cell lines have been derived that exhibit asymmetric cell kinetics in response to controlled expression of the wild-type murine p53 and these p53 model cell lines have been used to define cellular mechanisms that regulate asymmetric cell kinetics.

In addition to p53, the rate-limiting enzyme of guanine nucleotide biosynthesis, type II inosine-5'-monophosphate dehydrogenase (IMPDH II) is an important determinant of asymmetric cell kinetics. IMPDH II catalyzes the conversion of IMP to xanthosine monophosphate (XMP) for guanine ribonucleotide biosynthesis. This enzymatic reaction is rate-determining for the formation of the next metabolite in the pathway, guanine monophosphate (GMP), from which all other cellular guanine nucleotides are derived. Accordingly, high levels of guanine ribonucleotides (rGNPs) promote symmetric cell kinetics, whereas low levels of rGNPs promote asymmetric cell kinetics. Conditionally suppressing asymmetric cell kinetics can be achieved by enhancing guanine ribonucleotide biosynthesis, e.g., supplementing the culture media with guanine ribonucleotide precursors such as xanthosine (Xs), hypoxanthine (Hx) or xanthine (Xn), thereby expanding cellular pools of rGNPs.

Mechanisms which function downstream of the rGNPs to regulate cell kinetics (i.e., asymmetric versus symmetric) can also be used to conditionally suppress asymmetric cell kinetics. These mechanisms include both genetic and/or pharmacological approaches, analogous to those described in detail herein. For example, one can enhance expression of a protein downstream of the rGNP biosynthesis pathway, if that protein promotes symmetric cell kinetics. Alternatively, one can down regulate the expression of a protein downstream of the GNP pathway, if it promotes asymmetric cell kinetics.

Asymmetric cell kinetics, a characteristic of tissue stem cells, has been used to successfully isolate tissue stem cells (Lee H S, et al., Biotechnol Bioeng. 2003, 83:760-71). In the examples, the SACK-R cell strains were obtained by culturing the adult pancreatic islet cells in a tissue culture medium (e.g., DMEM, RPMI, etc.) supplemented with Xn prior to culturing in a medium known for cloning and culturing pluripotent stem cells in the presence of a STO feeder cell layer. The medium known for cloning and culturing pluripotent stem cells was also supplemented with Xn for greater reprogramming efficiency. Only Xn-responsive SACK strains (SACK-R), which show a significant reduction in culture growth rate upon removal of Xn due to a shift to asymmetric cell kinetics, yielded pluripotent stem cell-like colonies, e.g., having ESC-like morphology and alkaline phosphatase activity. SACK-non-responsive (SACK-NR) cells, which grow at similar rates (due to symmetric self-renewal) with or without Xn supplementation, did not produce colonies in a medium known for cloning and culturing pluripotent stem cells. SACK-R strains have properties indicative of tissue-specific pancreatic stem cells; whereas SACK-NR strains have properties of neoplastically transformed pancreatic cell lines. While not wishing to be bound by theory, by supplementing the tissue culture medium with Xn, these SACK-R cell strains were selected for an enrichment of multipotent tissue stem cells.

Figure 8:
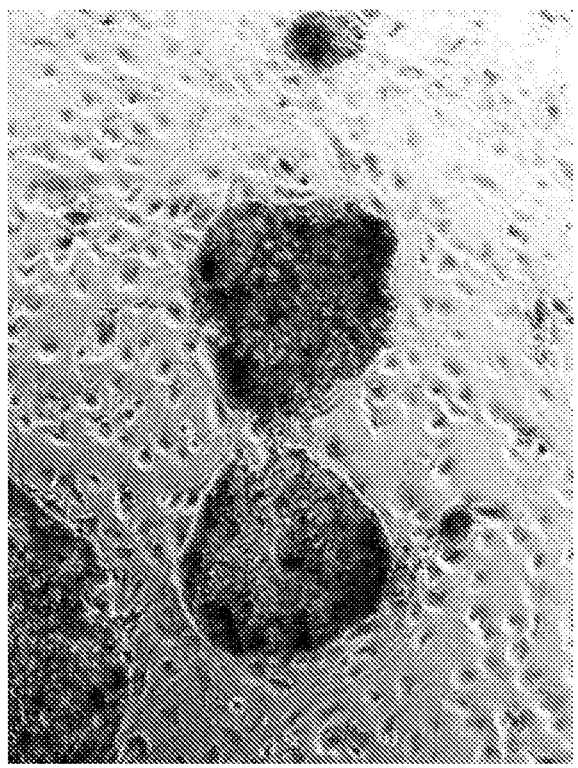
FIG. 8 shows that clonal iPSC-like cells derived from gene-free reprogramming of SACK-responsive, Pdx1-positive Panstra-25 pancreatic stem cells are alkaline phosphatase-positive. Shown is a micrograph of embryonic stem cell-like (ES), alkaline phosphate-positive (dark staining; AP+) clone #85 expanded in KOSR medium supplemented with xanthine (Xn).
Figure 9B:
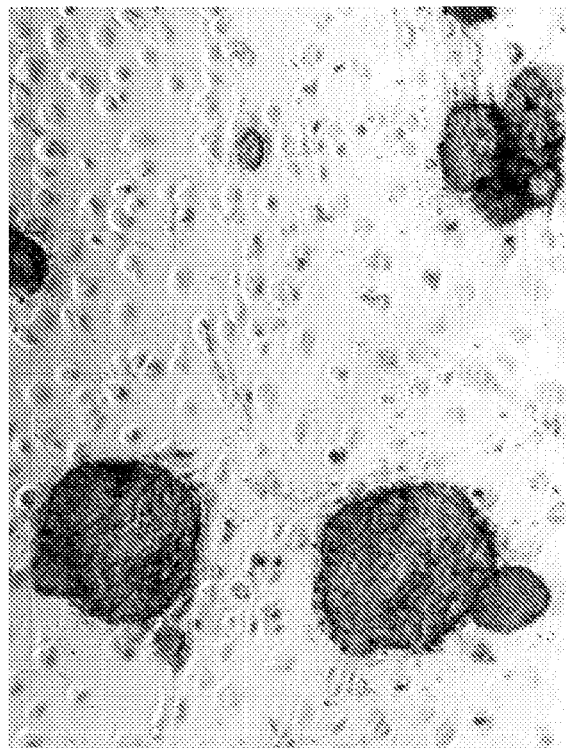
FIGS. 9A and 9B show that clonal iPSC-like cells derived from gene-free reprogramming of SACK-responsive, Pdx1-negative Panstra-12 pancreatic stem cells have a higher degree of alkaline phosphatase activity. Pdx1-negative cells are more primitive than Pdx1-positive cells. Shown are micrographs of embryonic stem cell-like (ESC-like), alkaline phosphate-positive (dark staining; AP+) clone #89 and clone #95 cell colonies expanded in KOSR medium supplemented with xanthine (Xn).
Figure 9A:
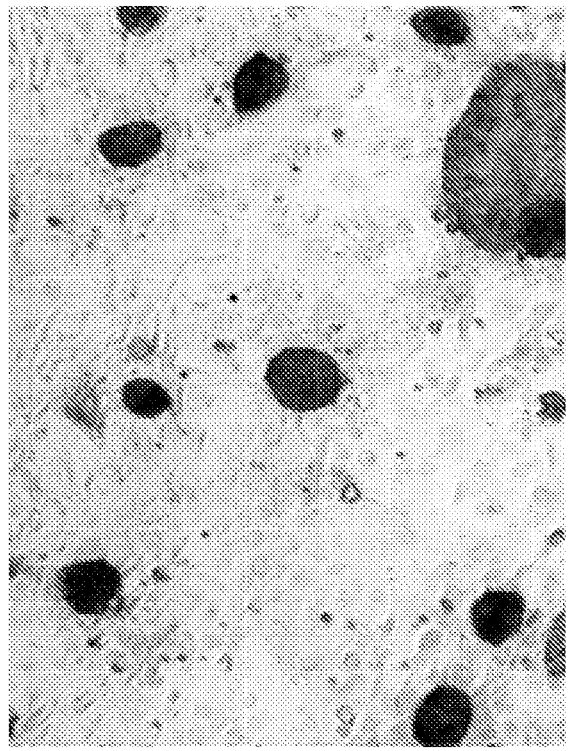
Figure 10B:
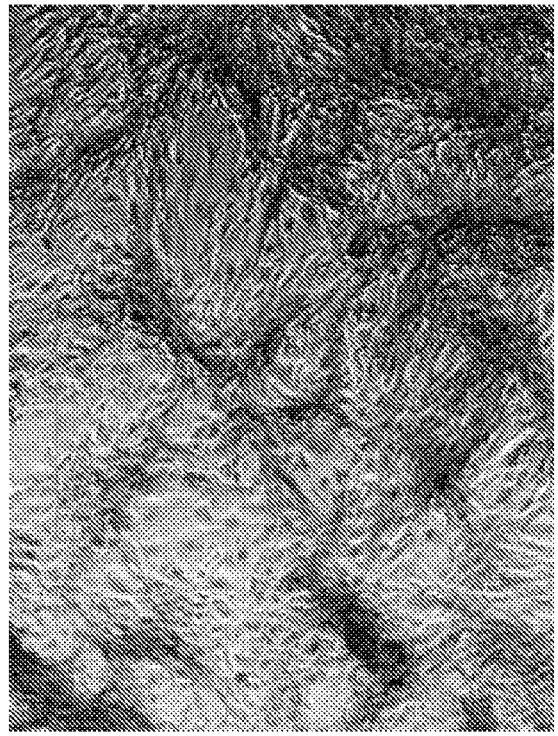
FIG. 10 shows that fibroblastic colonies produced in reprogramming cultures of SACK-responsive, Pdx1-negative Panstra-12 pancreatic stem cells are also alkaline phosphatase-positive. Shown are micrographs of fibroblast-like (Fl), alkaline phosphate-positive (dark staining; AP+) clone #49 colonies expanded in KOSR medium without xanthine (Xn) supplementation.
Figure 10A:
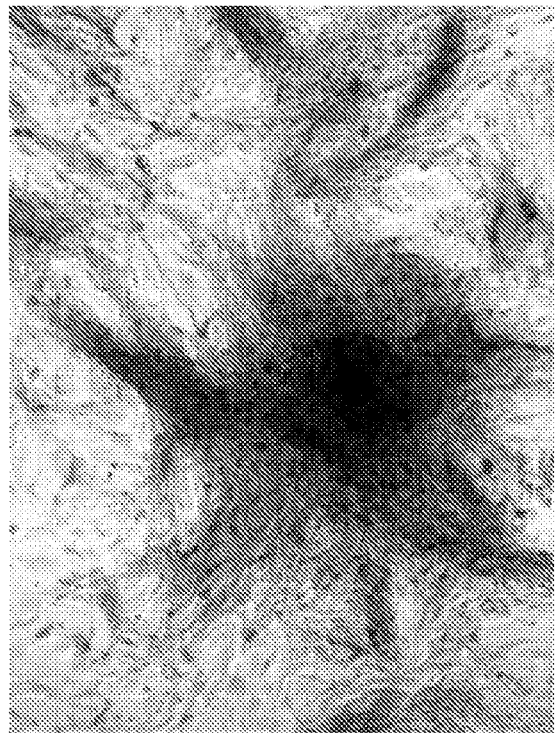

In the example, the differentiated cells are adult mouse pancreatic islet cells and Xn is the chemical compound used to suppress asymmetric cell kinetics (SACK). Cells treated with Xn can respond in either of two ways: (1) those that proliferate significantly slower (i.e., due to asymmetric cell kinetics) in the absence of Xn than in the presence of Xn are termed SACK-responsive (SACK-R); and (2) those that show no change in proliferative rate in the presence or absence of Xn are termed SACK non-responsive (SACK-NR). Using two different cell strains that were (1) derived from adult mouse pancreatic islets of xanthine phosphoribosyl transferase (XPRT)-transgenic mice and (2) expanded in medium that is supplemented with Xn to achieve SACK, the inventors found that two master transcription factor genes, Klf4 and c-Myc, show increased mRNA expression in the Xn-responsive (SACK-R) cells in the presence of Xn in the culture medium (Table 2). These Xn-treated and Xn-responsive cells then proceeded to express alkaline phosphatase, a known enzyme marker that is highly expressed in undifferentiated cells such as primordial germ cells (FIG. 8), after culture in media that support the proliferation of mouse pluripotent stem cells. Under these conditions, these Xn-expanded and Xn-responsive cells also multiply to form colonies that take on a clonal mouse embryonic stem cell-like morphology in culture, resembling a compact clump of round tiny cells, the clump having a smooth and well defined edge (FIG. 7B). The SACK-R cell strain Panstra-25, which displays tissue-specific stem cell properties and a greater cell kinetics response to Xn (i.e., SACK-responsive, SACK-R), also displays greater Xn-induced Klf4 and c-Myc expression (Table 2).

Isolation of Tissue Stem Cells

In one embodiment, for a population of single cells in suspension, the cells can be pelleted and washed by re-suspension in 30 ml of DMEM (high glucose, 4.5 mg/ml) supplemented with 10% dialyzed fetal bovine serum (JRH Biosciences). The cells are then pelleted at 200 g for 5 minutes at 4° C. After re-suspension in 30 ml of medium, 20 ml of the cell suspension (1×10exp7 viable cells) are placed into two 75-cm$^2$ culture flasks (10 ml each) and incubated overnight at 37° C. in a humidified incubator with a 5% $CO_2$ atmosphere to allow the attachment of cells.

Attached cells in the two flasks are removed with trypsin, combined into 20 ml of the medium, and pelleted at 200 g for 5 minutes at 4° C. The cells are then re-suspended in 20 ml medium, and the viable cell number determined by the trypan blue exclusion test. Cells are then diluted to a density of 20 viable cells per ml in same culture medium containing either 200 µM or 400 µM xanthosine or any of the described guanine nucleotide precursor. Aliquots of 100 µl of the diluted cells were pipeted into 96-well culture plates (i.e., giving an expected average of 2 cells per well).

Seeded 96-well plates are incubated at 37° C. in a humidified incubator with a 5% $CO_2$ atmosphere. Two weeks later, wells with single epithelioid cell colonies are detected by phase microscopy. The culture medium is aspirated from these wells; the cells are washed briefly with 0.2 ml phosphate-buffered saline; and 50 µl of Cell Dissociation Solution (Sigma Cat. # C5914) is added. After a period of 5-minute incubation at 37° C. in a humidified incubator with a 5% $CO_2$ atmosphere, 0.2 ml of the respective Xs-containing medium is added. The cells are gently dissociated with a 1-ml micropipette and then transferred to a well of a 24-well culture plate containing 5 ml Xs-containing medium.

The culture medium is changed the next day after transfer and thereafter every 2 days until wells are 20-70% confluent. Subsequently, ½-standard strength trypsin is used to transfer cells sequentially from 6-well plates, to 25-cm$^2$ culture flasks, and finally to 75-cm$^2$ culture flasks. Transfers can be performed when culture vessels were 20-80% confluent. The next day after each transfer, the medium is replaced with fresh Xs-containing medium, and thereafter it is replaced every 2 days. After reaching the 75-cm$^2$ flask stage, cells can be maintained in normal Xs-containing medium with 1:3 splits when they reached 80% confluency. Thereafter, for routine culture, all somatic stem lines are maintain with 1:20 to 1:5 splits when they reached ≥80% confluency.

In one embodiment, early passage cells were cryo-preserved by re-suspension in 70% DMEM (high glucose)/20% fetal bovine serum/10% DMSO. The cells from an 80% confluent 75-cm$^2$ culture flask can be re-suspended in 4.5 ml of freezing medium and frozen as 1.5-ml aliquots. Cell suspensions are placed in a Styrofoam box at −80° C. overnight and then transferred to liquid nitrogen for long-term preservation.

For a population of cells obtained from a tissue, first the cells obtained from donor tissue are dissociated into individual cells from the connecting extracellular matrix of the tissue. Tissue is removed using a sterile procedure, and the cells are dissociated using any method known in the art including treatment with enzymes such as dispase, collagenase, and the like, or by using physical methods of dissociation such as with a blunt instrument or mincing with a sharp instrument.

Dissociation of cells can be carried out in any acceptable medium, including tissue culture medium. The dissociated stem cells can be placed into any known culture medium capable of supporting cell growth, including DMEM, RPMI, HEM, F-12, and the like, containing supplements which are required for cellular metabolism such as glutamine and other amino acids, vitamins, minerals and useful proteins such as transferrin and the like. Medium can also contain antibiotics to prevent contamination with yeast, bacteria and fungi such as penicillin, streptomycin, gentamicin and the like. In some cases, the medium can contain serum derived from bovine, equine, chicken, human and the like. Serum can contain purine nucleotide precursors such as xanthine, hypoxanthine, or other compounds which enhance purine nucleotide biosynthesis, although generally at levels below the effective concentration to suppress asymmetric cell kinetics. Thus, preferably a defined, serum-free culture medium is used, as serum contains unknown components (i.e. is undefined). Preferably, if serum is used, it has been dialyzed to remove nucleotide precursors. A defined culture medium is also preferred if the cells are to be used for transplantation purposes. A particularly preferable culture medium is a defined culture medium comprising a mixture of DMEM, F12, and a defined hormone and salt mixture. As indicated herein, by including a compound such as guanine ribonucleotide precursor (e.g., Xs, Xn, Hx etc) at sufficiently high concentration, asymmetric cell kinetics are suppressed. Thus, the effect of division by differentiated transit cells, which results in the diluting of the stem cells, is reduced.

The culture medium can be supplemented with a proliferation-inducing growth factor(s). As used herein, the term "growth factor" refers to a protein, peptide or other molecule having a proliferative, differentiation, viability, or division arrest effect on on any type of cell in the culture, tissue stem cell or otherwise. Growth factors that can be used include any proliferation factor that promotes or supports cell division, including molecules that bind to a receptor on the surface of the cell. Preferred proliferation-inducing growth factors include EGF, amphiregulin, acidic fibroblast growth factor ($\alpha$FGF or FGF-1), basic fibroblast growth factor (bFGF or FGF-2), transforming growth factor alpha (TGF$\alpha$), and combinations thereof. Growth factors are usually added to the culture medium at concentrations ranging between about 1 ng/ml to 1 microg/ml. Concentrations between about 1 to 100 ng/ml are usually sufficient. Simple titration experiments can be easily performed to determine the optimal concentration of a particular growth factor.

In addition to proliferation-inducing growth factors, other growth factors can be added to the culture medium to influence cell cycle arrest, viability, and differentiation of the cells. These include NGF, platelet-derived growth factor (PDGF), thyrotropin releasing hormone (TRH), transforming growth factor betas (TGF$\beta$s), insulin-like growth factor (IGF-1) and the like.

In other embodiments, tissue stem cells can be isolated and cultured in suspension or on a fixed substrate. One particularly preferred substrate is a hydrogel, such as a peptide hydrogel, as described below and in U.S. Pat. No. 7,449,180, PCT/US2002/003607, and U.S. Provisional application No. 60/305,379. These references are hereby incorporated by reference in their entirety. However, certain substrates tend to induce differentiation of certain stem cells. Thus, suspension cultures are preferable for such stem cell populations. Cell suspensions can be seeded in any receptacle capable of sustaining cells, particularly culture flasks, cultures plates, or roller bottles, more particularly in small culture flasks such as 25 $cm^2$ cultures flasks. In one preferred embodiment, cells are cultured at high cell density to promote the suppression of asymmetric cell kinetics.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C.

Cells are preferably cultured for 3-30 days, preferably at least about 7 days, more preferably at least 10 days, still more preferably at least about 14 days. Cells can be cultured substantially longer. They can also be frozen using known methods such as cryo-preservation. When they are needed, the frozen cells are then thawed and used.

Culture Media

Culture media suitable for the in vitro culturing of cells according to the practice described herein are well known in the art. Such culture media include but are not limited to high glucose Dulbecco's Modified Eagles Medium (DMEM) with L-Glutamine which is well known and readily available commercially. The media can be supplemented with recombinant human basic fibroblast growth factor (rhbFGF) and contain sera, such as human serum, and antibiotics. Cell cultures are maintained in a $CO_2$ atmosphere, e.g., 5% to 12%, to maintain pH of the culture fluid, and incubated at 37° C. in a humid atmosphere. Suitable chemically defined serum-free media are described in U.S. Ser. No. 08/464,599 and WO96/39487, and "complete media" are described in U.S. Pat. No. 5,486,359 and these are hereby incorporated by reference in their entirety. Chemically defined medium comprises a minimum essential medium such as Iscove's Modified Dulbecco's Medium (IMDM) (Gibco), supplemented with human serum albumin, human Ex Cyte lipoprotein, transferrin, insulin, vitamins, essential and non essential amino acids, sodium pyruvate, glutamine and a mitogen. These media stimulate cell growth without differentiation. As used herein, a mitogen refers to an agent that stimulates cell division of a cell. The agent can be a chemical, usually some form of a protein that encourages a cell to commence cell division triggering mitosis. Other examples of culture medium include RPMI 1640, Iscove's modified Dubelcco's media (IMDM), and Opti-MEM SFM (Invitrogen Inc.).

The formulation of standard DMEM/F-12 is as follows: calcium chloride $2H_2O$ 0.154 g/L, cupric sulfate $H_2O$ 0.0000013 g/L, ferric nitrate $9H_2O$ 0.00005 g/L, ferrous sulfate $7H_2O$ 0.000417 g/L, magnesium chloride $6H_2O$ 0.0612 g/L, magnesium sulfate 0.04884 g/L, potassium chloride 0.3118 g/L, sodium chloride 6.996 g/L, sodium phosphate dibasic 0.07102 g/L, sodium phosphate monobasic 0.0543 g/L, zinc sulfate $7H_2O$ 0.000432 g/L, amino Acids: L-alanine 0.00445 g/L, L-arginine HCl 0.1475 g/L, L-asparagine $H_2O$ 0.0075 g/L, L-aspartic acid 0.00665 g/L L-cystine 2HCl 0.03129 g/L, L-cysteine HCl $H_2O$ 0.01756 g/L, L-glutamic acid 0.00735 g/L, L-glutamine 0.365 g/L, glycine 0.01875 g/L, L-histidine HCl $H_2O$ 0.03148 g/L, L-isoleucine 0.05447 g/L, L-leucine 0.05905 g/L, L-lysine HCl 0.09125 L-methionine 0.01724 L-phenylalanine 0.03548 L-proline 0.01725 L-serine 0.02625 L-threonine 0.05345 g/L, L-tryptophan 0.00902 g/L, L-tyrosine 2Na $2H_2O$ 0.05579 g/L, L-valine 0.05285 g/L; vitamins: biotin 0.0000035 g/L, choline chloride 0.00898 g/L, folic acid 0.00266 g/L, i-inositol 0.0126 g/L, nicotinamide 0.00202 g/L, D-pantothenic acid Ca 0.00224 g/L, pyridoxine HCl 0.000031 g/L, pyridoxal hydrochloride 0.002 g/L, riboflavin 0.000219 g/L, thiamine HCl 0.00217 g/L, vitamin B12 0.00068 g/L; other: D-glucose 3.15 g/L, hypoxanthine (Na) 0.0021 g/L, linoleic acid 0.000042 g/L, lipoicacid 0.000105 g/L, phenol red 0.0081 g/L, putrescine HCl 0.000081 g/L, pyruvic acid, sodium salt 0.055 g/L, thymidine 0.000365 g/L.

The commercial formulation is supplemented with 3700 mg/l of sodium bicarbonate and 10 ml/l of a 100× (100 times concentrated) antibiotic-antimycotic cocktail containing 10,000 units of penicillin, 10,000 µg of streptomycin, and 25 µg of amphotericin B/ml utilizing penicillin G (sodium salt), streptomycin sulfate, and amphotericin B (FUNGIZONE™) in 0.85% saline.

Other culture media supplements include platelet rich plasma supplemented with heparin (2 U/ml); the basic fibroblast growth factor (bFGF) and recombinant human basic fibroblast growth factor (rhubFGF).

A medium capable of supporting reprogramming of cells (i.e. reprogramming media) or alternatively media capable of supporting the growth of pluripotent cells is any medium that is known and used in the art for reprogramming differentiated cells to become induced pluripotent stem cells and for culture maintenance of embryonic stem cells and iPSCs. The name, "reprogramming medium" does not express or imply that a medium itself induces reprogramming independent of other rate-determining factors (e.g., transcription factors and, in the instant invention, tissue stem cell phenotype), instead only that it is optimized for the maintenance of reprogrammed cells. In general, reprogramming media are equivalent to media for maintenance of pluripotent stem cells like embryonic stem cells. In various embodiments, the reprogramming medium comprises leukemia inhibitory factor (LIF). In some embodiments, the reprogramming medium comprises antibiotics, e.g. penicillin-streptomycin, gentamycin, and amphotericin-B. In some embodiments of the invention, the reprogramming medium can contain at least one growth factor essential for iPSC cell culture, such as bFGF, FGF-2, TGF-β and insulin.

In accordance with an aspect of the invention, any serum-free embryonic stem cell (ES) medium can also be used as a reprogramming medium for cloning and culturing induced pluripotent cells (iPSCs). An exemplary serum-free ES medium can comprise serum replacement such as KNOCKOU™ serum replacement from Invitrogen, non-essential amino acid, L-glutamine, β-mercaptoethanol or a combination thereof. In one embodiment, serum-free ES medium can be prepared with about 80% KNOCKOUT™ DMEM, about 20% serum replacement, about 1% non-essential amino acids, about 1 mM L-glutamine, and about 0.1 mM β-mercaptoethanol. In some embodiments, human bFGF can be added to the serum-free ES medium.

Other non-limiting examples of the reprogramming media that can be used for the purpose of the invention include STEMPRO® hESC SFM, KNOCKOUT™ D-MEM, KNOCKOUT™ DMEM/F12, and KNOCKOUT™ SR XenoFree medium (all from Invitrogen); ES-CULT® medium (from StemCell Technologies); mouse embryonic fibroblast conditioned media and human feeder cell conditioned media (from R & D Systems); and STEMLINE® family of media from Sigma-Aldrich.

Examples of reprogramming media include but are not restricted to only these:
(1) a medium comprising DMEM, FBS, L-glutamine, Non-Essential Amino Acids, Penicillin/Strep, HEPES, 2-beta ME, leukemia inhibitory factor (LIF) 1000 U/ml;
(2) a medium comprising DMEM/F12, KSR, L-glutamine, Non-Essential Amino Acids, Pen/Strep, 2-beta ME;

In one embodiment, the reprogramming media comprises FBS or KNOCKOUT™ serum replacement reagent by INVITROGEN™ (KSR) that is used in the range from 10-20%.

In one embodiment, the medium contains 2 mM L-glutamine, $1 \times 10^{-4}$ non-essential amino acids, 50 units of penicillin, 50 mg/ml streptomycin and $1 \times 10^{-4}$ 2-beta ME.

In one embodiment, the medium is used in conjunction with a STO mouse fibroblast, mouse embryo fibroblast (MEF) or SNL feeder cell layer. These cells are rendered mitotically inactive by treatment with gamma-irradiation. SNL 76/7, established by Dr. Allan Bradley (1990, Cell 62:1073-1085), is clonally derived from a mouse fibroblast STO cell line transformed with neomycin resistance and murine LIF genes. SNL can be used as a feeder cell for ES cell growth without supplementing the medium with exogenous LIF, and it also has been recently used in mouse or human iPS culture (Okita, K. et al., 2007, Nature 448:313-317; Takahashi K. et al., 2007, Nat. Protoc. 2:3081-9). These references are hereby incorporated by reference in their entirety.

In one embodiment, the medium is supplemented with mitomycin C (10 µg/ml).

As used herein, "reprogramming condition" comprises at the minimum a medium capable of supporting the dedifferentiation of cells and STO mouse fibroblast, mouse embryo fibroblast (MEF) or SNL feeder cell layer, wherein leukemia inhibitory factor (LIF) 1000 U/ml is added if SNL feeder cell layer is not used.

Unless otherwise explained, all technical and scientific terms used herein have the same meaning as commonly understood by one of ordinary skill in the art to which this disclosure belongs.

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987)); Current Protocols in Molecular Biology (CPMB) (Fred M. Ausubel, et al. ed., John Wiley and Sons, Inc.); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); and Animal Cell Culture Methods (Methods in Cell Biology, Vol. 57, Jennie P. Mather and David Barnes editors, Academic Press, 1st edition, 1998) which are all incorporated by reference herein in their entirety.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or media conditions used herein should be understood as modified in all instances by the term "about." The term "about" when used in connection with percentages may mean±1%.

The singular terms "a," "an," and "the" include plural references unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention can be defined in any of the following alphabetized paragraphs:

[A] A method of reprogramming a population of tissue stem cells comprising the steps of:
  a. contacting a population of cells comprising tissue stem cells with xanthine (Xn) in a culture medium;
  b. culturing the population of cells comprising tissue stem cells of step a in the culture medium containing Xn; and
  c. culturing the population of cells comprising tissue stem cells from step b in a medium capable of supporting the maintenance of pluripotent cells or reprogrammed cells.

[B] The method of paragraph [A], wherein the population of tissue stem cells of step b undergo suppression of asymmetric cell kinetics in the presence of Xn, thereby increasing the proportion of stem cells in the population of cells.

[C] The method of paragraph [A] or [B], wherein the tissue stem cell is a Xn-responsive cell.

[D] The method of any one of paragraphs [A]-[C], wherein Xn is included in the medium capable of supporting the maintenance of pluripotent cells or reprogrammed cells.

[E] A method of reprogramming a tissue stem cell comprising the steps of:
  a. clonally isolating a tissue stem cell from a population of cells; and
  b. contacting the isolated tissue stem cell with xanthine (Xn) in a medium capable of supporting the maintenance of pluripotent cells or reprogrammed cells.

[F] The method of paragraph [E], wherein the tissue stem cell is isolated by suppression of asymmetric kinetics using Xn.

[G] A method of reprogramming a tissue stem cell comprising the steps of:
  a. clonally isolating a tissue stem cell from a population of cells in a culture medium comprising xanthine (Xn); and
  b. culturing the isolated tissue stem cell in a medium capable of supporting the maintenance of pluripotent cells or reprogrammed cells.

[H] The method of paragraph [G], wherein the tissue stem cell is isolated by suppression of asymmetric kinetics in the presence of Xn.

[I] The method of paragraphs [G] or [H], wherein the medium capable of supporting the maintenance of pluripotent cells or reprogrammed cells comprised Xn.

[J] The method of any one of paragraphs [A]-[H], wherein the concentration of xanthine is about 1 mM.

[K] The method of any one of paragraphs [A]-[J], wherein the tissue stem cell is reprogrammed to a pluripotent state.

[L] The method of any one of paragraphs [A]-[K], wherein the tissue stem cell is selected from the group of liver stem cells, hair follicle stem cell and pancreas stem cell.

[M] A method of reprogramming a tissue stem cell comprising contacting a tissue stem cell with xanthine in a medium capable of supporting the maintenance of pluripotent cells or reprogrammed cells, wherein the tissue stem cell is responsive to xanthine.

[N] A method for increasing the efficiency of reprogramming somatic cells or tissue stem cells comprising contacting the cell to be reprogrammed with a medium capable of supporting the maintenance of pluripotent cells or reprogrammed somatic cells wherein the medium comprises Xn.

[O] The method of paragraph [M] or [N], wherein the concentration of xanthine is about 1 mM.

[P] The method of any one of paragraphs [M]-[O], wherein the tissue stem cell is reprogrammed to a pluripotent state.

[Q] The method of any one of paragraphs [M]-[P], wherein the tissue stem cell is selected from the group of liver stem cells, hair follicle stem cell and pancreas stem cell.

This invention is further illustrated by the following example, which should not be construed as limiting. The contents of all references cited throughout this application, as well as the figures and table are incorporated herein by reference.

EXAMPLES

The invention is a method for efficient production of clonal pluripotent stem cells without using gene-transfer or protein-transfer. The derived cells have properties akin to those described for induced pluripotent stem cells ("iPSCs"), which are produced by either gene transfer or, more recently, by protein transfer.

The method is an original pharmacological procedure for producing pluripotent stem cells. Cell strains derived in xanthine (Xn)-supplemented medium, by the method of suppression of asymmetric cell kinetics (SACK), were cultured in commercial media specified for the culture and/or production of pluripotent stem cells such as embryonic stem cells and iPSCs. Approximately 150,000 cells were plated on confluent STO cell feeders (i.e., mouse embryonic fibroblasts pre-treated with mitomycin C) in 10-cm culture dishes. In 2 weeks, iPSC-like cell colonies were detected.

To establish clonal strains, single colonies were picked, cultured in individual wells, and expanded for further study and cryo-preservation. A high fraction of the derived cell clones have morphological and biochemical properties indicative of iPSC cells.

In previously reported methods, the commercial media alone did not convert cells into iPSCs without either transfer of 2-4 pluripotency-inducing master transcription factor genes or transfer of 3-4 pluripotency-inducing master transcription factor proteins. The present method achieves iPSC production at comparable or better rates than the transfer methods, respectively. Moreover, including the SACK agent Xn in the iPSC media at 1 mM concentration increased the conversion rate approximately 3-fold.

In the example, a model system of rodent cells was used. These rodent cells were derived from transgenic mice carrying the xanthine phosphoribosyl transferase (XPRT) gene, to ensure that all types of cells in the examples are efficient in uptaking and metabolizing Xn. The XPRT enable the transgenic mice to uptake and metabolize Xn wherein Xn serves as a guanine ribonucleotide precursor. While most mammalian cells can utilize, i.e., uptake and metabolize, Xn, they may do so at different rates and efficiencies. Since the present method requires the use of guanine ribonucleotide precursor to achieve SACK, the proof-of-principle example was performed in model cells that can definitely utilize Xn and exhibit SACK in the presence of Xn, cells from the XPRT transgenic mice. The goal of the XPRT mice was to provide ideal SACK responsiveness for all types of tissue specific stem cells by insuring the critical metabolism of a SACK agent with no entry barriers, Xn. Xs and Hx require the expression of specific transmembrane transporters for efficient cell entry, which might not be present on some types of stem cells of interest. Xn can enter via ubiquitous purine base transporters and cross directly through the membrane by efficient diffusion. The transgenic rodent SACK-R somatic cells described herein serve as an example of a mammalian cell that is SACK-R, can uptake and metabolize Xn, wherein Xn serves as a guanine ribonucleotide precursor. Xn is the chemical agent used to suppress asymmetric cell kinetics (SACK) tissue stem cells found in preparations of differentiated adult mouse pancreatic islet cells.

Example 1

Characterization of the Tissue Stem Cell Properties of SACK-Responsive Pancreatic Stem Cell Strains Several xanthine nucleus compounds have been defined as SACK agents (Sherley, 2002). By preventing p53/IMPDH-related reduction in rGNP pools, SACK agents shift explanted tissue stem cells from asymmetric cell kinetics to symmetric cell kinetics, and thereby promote their exponential expansion. Three purine nucleotide precursors have been shown to have this ability due to their entry points into the rGNP biosynthetic pathway (FIG. 1).

Hypoxanthine (Hx) is postulated to increase flux through the regulated pathway by increasing the level of IMP, the IMPDH substrate. Xanthine (Xn) and xanthosine (Xs) are postulated to bypass the point of p53 regulation altogether by promoting formation of XMP, the product of the IMPDH reaction. Consistent with their predicted effects on p53-induced asymmetric cell kinetics, all three compounds have been shown to induce p53-expressing model cell lines to reversibly shift from asymmetric cell kinetics to symmetric cell kinetics (Sherley, 1991; Sherley et al., 1995; Liu et al., 1998). When tissue cell preparations are cultured in the presence of one or more of these compounds, tissue-specific stem cells selectively multiply exponentially as a result of a SACK-dependent reversible shift from asymmetric cell kinetics to symmetric cell kinetics. The resulting tissue stem cell strains have a greatly reduced frequency of cell variants with stably disrupted asymmetric cell kinetics (e.g., p53 mutant cells), because SACK expansion overcomes the growth advantage of cells that acquire growth-activating mutations.

Xanthine phosphoribosyl transferase (XPRT)-transgenic mice were developed to expand the tissue range and efficiency of SACK expansion of murine tissue stem cells. These mice were designed to provide effective SACK action uniformly in all mouse tissues. XPRT converts xanthine (Xn) directly into the rate-limiting IMPDH product xanthosine monophosphate (XMP; See FIG. 1). Xn partitions readily across the cell plasma membrane. So, by developing mice with a germline XPRT transgene expressed from a ubiquitous promoter, tissue stem cells in all types of tissues might be effectively expanded by SACK with Xn.

The SACK approach was used to establish several stable cell strains from the pancreas of adult XPRT-transgenic mice. Pancreatic islets were isolated by standard procedures and plated on gelatin-coated plates (10 islets per well of 24-well culture plates) in control medium (DMEM, 10% dialyzed fetal bovine serum, 1 ng/ml keratinocyte growth factor [KGF]) or medium supplemented to 1 mM concentration with Xs, Hx, or Xn. Even though Xn was the preferred SACK agent by design, because of purine interconversion reactions, Xs and Hx can also act as effective SACK agents with XPRT-expressing tissue stem cells. After 3 weeks of culture, expanded cultures were cryo-preserved and single-cell cloned to establish clonal pancreatic cell strains. The establishment of stable cell strains required both islets from XPRT-mice and SACK-agent supplemented culture medium. No pancreas-derived cells grew from non-transgenic mice whether or not SACK agents were supplemented; and no pancreas-derived cells grew from XPRT-transgenic mice when only control medium was used.

The SACK-derived clonal pancreatic cell strains have properties of either beta-cell precursors (Pdx1+) or more primitive pancreatic cells (Pdx1−). In the colony formation analyses, three hundred (300) cells were plated in replicate (n=3) 30-mm diameter culture dishes. Twenty-four hours later, the culture medium was replaced with the medium supplemented with SACK agents as indicated. Ten days later, plates were stained with crystal violet and colonies counted. Xs, xanthosine; Xn, xanthine; Hx hypoxanthine.

Figures 2A, 2B:
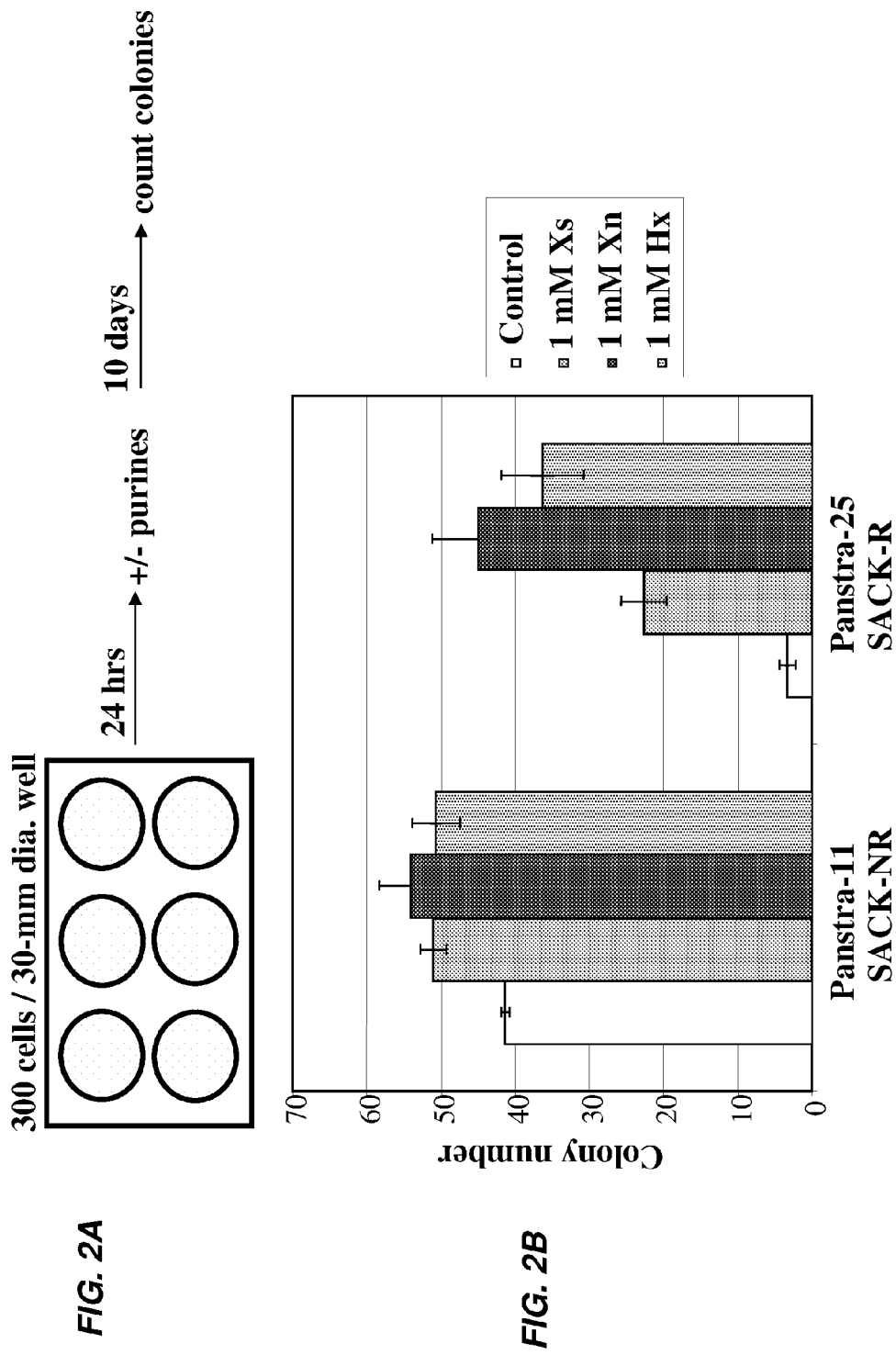
FIG. 2A shows the general schematics of a colony formation analyses with mouse SACK-responsive (R) Panstra-25 cells or non-responsive (NR) Panstra-11 cells that are derived mouse pancreatic cell strains. Cells were plated at colony forming density in SACK-free culture medium (Control) or culture medium supplemented to 1 mM concentration with the SACK agents xanthosine (Xs), xanthine (Xn), or hypoxanthine (Hx).
FIG. 2B is a histogram of a colony formation analyses with SACK-responsive (R) Panstra-25 cells or non-responsive (NR) Panstra-11 cells in culture media supplemented to 1 mM concentration with the SACK agents xanthosine (Xs), xanthine (Xn), or hypoxanthine (Hx). Error bars indicate the sample standard deviation for analyses performed in triplicate.

As shown in FIG. 2, there are two distinct types of cell strains in terms of cell kinetics, highly SACK-responsive (SACK-R) and SACK-non-responsive (SACK-NR). These two different cell kinetics types arise despite the fact that no cell strains can be expanded in the absence of a SACK agent.

In order to study the formation of islet-like clusters after induction of differentiation in Xn-free medium, pancreatic beta-cell differentiation was induced by plating the cells on a poly-D-lysine substrate and changing growth medium to medium containing 1% dialysed fetal bovine serum, 20 ng/mL epidermal growth factor (EGF), 10 mM nicotinamide, and 25 mM glucose. FIG. 3B shows cells three days after the induction of differentiation. Upper panels, routine culture conditions with Xn supplementation, no expressed insulin was detectable in the presence of Xn; lower panels, Xn-free differentiation conditions. Insulin was expressed in cells differentiated in Xn-free conditions after three days. The expression of insulin was detected by immunofluorescence (data not shown). DAPI, detection of corresponding cell nuclei. In addition to long-term self-renewal in Xn-supplemented medium, SACK-R strains can be induced to undergo pancreatic islet differentiation when Xn is removed as demonstrated by the expression of insulin. These properties of self-renewal in an undifferentiated state and the ability to produce differentiated pancreatic cells define the SACK-R strains as pancreatic tissue stem cells.

As a further validation of the tissue-specific stem cell phenotype of SACK-R strains, their in vivo tissue homing properties were investigated. Stable yellow fluorescent protein (YFP)-expressing clones of SACK-R and SACK-NR strains were derived such that the strains maintained their original cell kinetics distinction. When these cells were injected into the peritoneal cavity of congenic mice, their behavior was remarkably different. SACK-NR cells were highly tumorigenic, producing large YFP-expressing tumors in the pancreas, lungs, liver, kidneys, and spleen within 2 months.

These tumors had features of insulinomas. The transformed phenotype of SACK-NR cell strains is likely to account for their non-responsiveness to SACK agents. Rodent cells typically undergo neoplastic transformation after prolonged growth in culture as a result of p53-related gene mutation. In the absence of intact p53 regulation, SACK agents are predicted to have no effect on cell growth. The fact that SACK-R strains are non-tumorigenic confirms the prediction that SACK agents can promote the growth of non-transformed, tissue-specific stem cell clones.

In contrast to SACK-NR strains, there was no grossly detectable growth of the SACK-R cells in mice. However, on whole-mount fluorescent microcopy of their pancreases, fluorescent cell clusters were observed in transplanted animals that were not detectable in non-transplanted animals (data not shown). YFP-fluorescent cell clusters detected in the pancreas of mice transplanted with YFP-marked SACK-R pancreatic stem cell strains.

PCR analyses performed to detect YFP DNA sequences showed that the transplanted cell DNA was found primarily in the pancreas and spleen, with the frequency of pancreas detection being 2-fold greater (Table 1). Given that this assay looks at cell DNA and not necessarily intact cells, the spleen detection could be due to clearance of dead cells in the spleen, as no YFP fluorescence was observed there in mice transplanted with SACK-R cell strains. Even though YFP DNA was detected in all tissues examined from SACK-NR-transplanted mice, the relative levels of detection from one tissue to the next were qualitatively similar to SACK-R transplanted mice.

These studies indicate that SACK-derived tissue-specific stem cells home to their own niches in normal mice. The recipient mice were transplanted without any prior adverse treatment. Thus, the findings also indicate that there are physiological pathways available for their entry. A lymphatic route may have been used by SACK-R cells to gain access to the pancreatic parenchyma.

Example 2

Example of Gene Free iPSC Reprogramming Using Tissue-Specific Stem Cells and Xanthine, a SACK Agent All the described induced pluripotent stem cell (iPSC) reprogramming genes are detected in two cell strains derived with the suppression of asymmetric cell kinetics (SACK)-agent xanthine (Xn). The SACK strains were derived from pancreatic islets of adult xanthine phosphoribosyl transferase (XPRT)-transgenic mice. The derivation of such strains requires both the XPRT-transgenic genotype and Xn.

Two genes, Klf4 and Myc, show increased mRNA expression in response to culture in Xn (Table 2). It is noteworthy that SACK strain Panstra-25, which displays tissue-specific stem cell properties and a greater cell kinetics response to Xn (i.e., SACK-responsive, SACK-R), also displays greater Xn-induced Klf4 and Myc expression.

Figure 6:
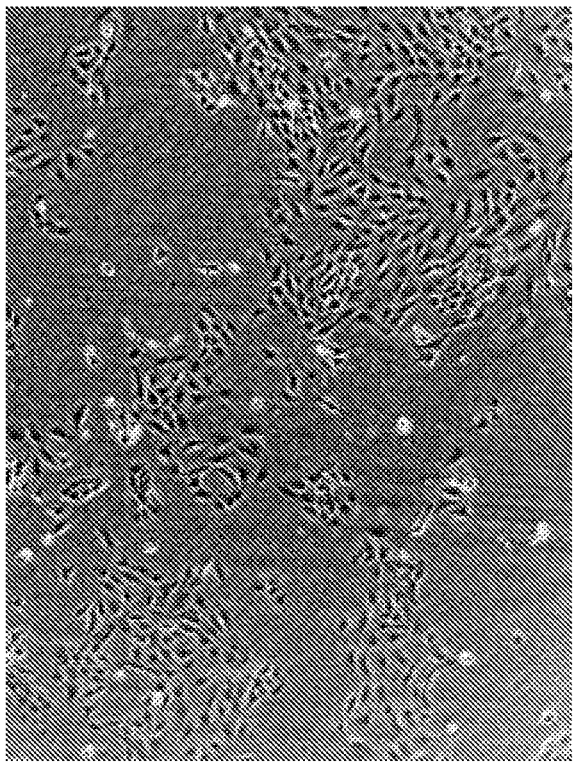
FIG. 6 shows the cell morphology and alkaline phosphate staining of SACK-responsive, Pdx1+Panstra-25 cells grown in maintenance culture conditions on gelatin-coated plates, 10% DFBS, 1 mM xanthine, i.e., not in reprogramming conditions or media. These SACK-responsive pancreatic stem cell strains grow as alkaline phosphate (AP)-negative epithelioid cells under routine cell culture conditions.

Tissue-specific stem cells (e.g., Panstra-25 and Panstra-12 mouse pancreatic stem cell strains in the instant example) were cultured on mitomycin C-treated STO cell monolayers in commercial embryonic stem cell medium supplemented with the purine salvage base xanthine at 1 mM concentration (FIG. 4). Within 2-3 weeks of culture under otherwise standard conditions, cell colonies with embryonic stem cell-like morphology developed (FIG. 7B). These colonies were removed by mild trypsin treatment, transferred to individual cell culture wells prepared with STO cell feeders, and expanded in the respective embryonic stem cell culture medium supplemented with 1 mM xanthine (FIG. 5). The expanded cell clones expressed alkaline phosphatase (FIG. 8), a biochemical biomarker for the pluripotent phenotype of embryonic stem cells and iPSC cells. In contrast, the initiating tissue-specific stem cells were alkaline phosphatase-negative and did not produce embryonic stem cell-like colonies (FIG. 6). The iPSC-like cell clones arose at efficiencies comparable to that of iPSC clones produced by gene-transfer (Tables 5 and 7). Xn supplementation increased the average production efficiency by as much as 3-fold (Table 6).

The data in this example indicate that both SACK-R and SACK-NR Panstra strains express "iPSC" genes. Klf4 and Myc are the highest expressed iPSC genes in the cells. For Klf4 and Myc, the detected expression is Xn-inducible; and the response was greater in a SACK-R Panstra strain compare to a SACK-NR strain. SACK-R strains also show a greater cell kinetics response to Xn.

At a low efficiency (estimated 0.02-0.07%) gene-free iPSC-like colonies (ESC-like colony morphology; AP+) were induced when two different SACK-R strains were cultured under iPSC culture conditions.

The derivation efficiency is comparable to reports using iPSC gene induction. The iPSC-like colonies can be expanded as cultures and cryopreserved. Of the two types of commercial media tested, KOSR medium gave the best results.

Unlike SACK-R strains, two tested SACK-NR strains did not produce iPSC-like colonies. A more primitive Pdx1-SACK-R strain yielded iPSC-like colonies at approximately 4 times the rate of a Pdx1+ SACK-R strain. In addition, the Pdx1− strain showed an average 3-fold higher rate of iPSC-like colony production (p=0.024) when supplemented with Xn.

The invention achieves the purpose of providing an efficient means of producing iPSCs without the use of gene-transfer, which has significant risks of introducing harmful genetic mutations (e.g., gene insertion; gene expression dysregulation; and point mutations and gene deletions in the case of retrotransposon excision strategies) or protein-transfer, which has a substantially lower efficiency. SACK agents, independently, may also be able to increase the efficiency of the other methods, as in the case of Xn for SACK-R-derived iPSCs.

Example 3

Differentiation Potency of Xn-Reprogrammed iPSC

In order to evaluate the differentiation potency of SACK-derived iPSC-like clones associated with tumor formation, selected SACK-derived iPSC-like clones were injected into immuno-deficient mice subcutaneously. Completely reprogrammed iPSCs form teratomas that include features characteristic of each of the three embryonic germ layers (ectoderm, endoderm, mesoderm). Two clones were selected from each of the SACK-R Panstra strains (−12 and −25) based on their high level of alkaline phosphatase activity. These clones had been derived and grown in conditions favorable for the expansion of mouse embryonic stem cells (ESCs) (STO feeder layers and Knockout Replacement Serum). Each clone was injected into two mice, behind each hind limb, at a level of 5 million cells per injection site. In parallel with these four SACK-derived iPSC-like clones, equal numbers of undifferentiated mouse ESCs (positive control) and the parental SACK-R Panstra stem cell strains (negative controls) were injected the same manner.

Subcutaneous tumors became visible in the mice injected with ESCs four weeks later. They were then harvested and fixed for histological analyses. Among all the other cells strains or clones injected, at six months after injection, only the iPSC-like cells produced from strain Panstra-12 cells (Pdx1-negative) gave rise to visible tumors. Along with a tumor originating from the ESCs, a tumor sample from each injected mouse was analyzed by histology exam for the presence of features indicative of each of the three germ layers. Three sections from each tumor, each at a different depth of the tumor, were stained with hematoxylin and eosin and evaluated by light microscopy. All tumor samples, including the one originating from the ESCs, exhibited histological features of two of the three germ layers, endoderm and mesoderm (FIGS. 11A and 11B). This finding showed that the Panstra-12 iPSC-like clones (of endodermal origin) were reprogrammed with the capacity to differentiate into mesodermal tissues.

In this analysis, ectodermal tissues were not detected in the positive control tumors derived from injected ESCs. This situation might occur because the ESC lines' ectodermal potential was lost at some point in the experimental procedures leading to the subcutaneous injections; or it may be that ectodermal tissues were below the detection limit of the histological sampling. The absence of ectoderm in the Panstra-12 iPSC-like clones could be the result of incomplete reprogramming; or the ectoderm might also have been below the detection limit of the histological sampling method used. In any event, the finding of mesodermal tissues in the tumors is a clear indication that a significant degree of reprogramming does in fact occur with SACK-derived Panstra adult stem cell strains without the use of gene or protein transfer.

REFERENCES

Liu, Y., Bohn, S. A., and Sherley, J. L. (1998) Inosine-5'-monophosphate dehydrogenase is a rate-determining factor for p53-dependent growth regulation. Mol. Biol. Cell 9, 15-28.
Sherley, J. L. (1991) Guanine nucleotide biosynthesis is regulated by the cellular p53 concentration. J. Biol. Chem. 266, 24815-24828.
Sherley, J. L. (2002) Asymmetric cell kinetics genes: The key to expansion of adult stem cells in culture. Stem Cells 20, 561-572.
Sherley, J. L., Stadler, P. B., and D. R. Johnson (1995) Expression of the wildtype p53 antioncogene induces guanine nucleotide-dependent stem cell division kinetics. Proc. Natl. Acad. Sci. 92, 136-140.

TABLE 1

Tissue Distribution of Transplanted SACK-derived Cells Detected by PCR

| Tissue | SACK STRAIN* | |
|---|---|---|
| | Panstra-11 SACK-NR | Panstra-25 SACK-R |
| Pancreas | 2/12 | 8/25 |
| Liver | 5/12 | 1/25 |
| Lung | 4/12 | 0/25 |
| Spleen | 10/12 | 4/25 |
| Kidney | 4/12 | 0/25 |
| Small Intestines | 1/12 | 0/25 |

*Number of positive mice/total mice transplanted

TABLE 2

Expression of reprogramming genes in SACK-derived mouse pancreatic cell strains (based on gene micro-array data)

| | Panstra-25 - Xn responsive | | Panstra-11-Xn Non-responsive | |
|---|---|---|---|---|
| Gene | Xn | Control | Xn | Control |
| Oct4 | 2.3 | 2.0 | 2.6 | 2.5 |
| Sox2 | 0.2 | 0.2 | 0.1 | 0.0 |
| Klf4 | 31.8 | 14.2 | 21.6 | 13.5 |
| Myc | 35.5 | 22.9 | 19.6 | 15.2 |
| Lin28 | 1.0 | 0.8 | 0.9 | 0.9 |

* Nanog absent from the microarray

TABLE 3

Only SACK-R Panstra Strains Exhibit Gene-Free iPSC Reprogramming

| Panstra Strain | SACK Agent | SACK Type | Pdx1 | iPSC |
|---|---|---|---|---|
| Panstra 11 | Xn | NR | (+) | No |
| Panstra 12 | Xn | R | (−) | Yes |
| Panstra 25 | Xn | R | (+) | Yes |
| Panstra 56 | Xn | NR | not done | No |

TABLE 4

Phenotypes of individual cell clones following expansion in respective medium (Strain Panstra-25)

| | Phenotype | | | |
|---|---|---|---|---|
| Condition | Fl, AP− | Fl, AP+ | ES, AP− | ES, AP+ |
| DFBS, control | 23/23 (100%) | 0/23 (0%) | 0/23 (0%) | 0/23 (0%) |
| DFBS, 1 mM Xn | 22/22 (100%) | 0/22 (0%) | 0/22 (0%) | 0/22 (0%) |
| hiFBS, control | 4/20 (20%) | 1/20 (5%) | 9/20 (45%) | 6/20 (30%) |
| hiFBS, 1 mM Xn | 5/19 (26%) | 1/19 (5%) | 10/19 (53%) | 3/19 (16%) |
| KOSR, control | 0/16 (0%) | 0/16 (0%) | 14/16 (87.5%) | 2/16 (12.5%) |
| KOSR, 1 mM Xn | 0/20 (0%) | 0/20 (0%) | 14/20 (70%) | 6/20 (30%) |

Fl = fibroblast-like morphology
ES = embryonic stem cell-like morphology
AP = alkaline phosphatase activity (positive colonies range from 5% to 60% positive cells)
ES, AP+ corresponds to iPSC state

TABLE 5

Estimated gene-free iPSC colony formation efficiency (%)
(Strain Panstra-25)

| Condition | Phenotype | | | |
|---|---|---|---|---|
| | Fl, AP− | Fl, AP+ | ES, AP− | ES, AP+ |
| DFBS, control | 0.061 | 0.000 | 0.000 | 0.000 |
| DFBS, 1 mM Xn | 0.059 | 0.000 | 0.000 | 0.000 |
| hiFBS, control | 0.011 | 0.003 | 0.024 | 0.016 |
| hiFBS, 1 mM Xn | 0.013 | 0.003 | 0.027 | 0.008 |
| KOSR, control | 0.000 | 0.000 | 0.037 | 0.005 |
| KOSR, 1 mM Xn | 0.000 | 0.000 | 0.037 | 0.016 |

Fl = fibroblast-like morphology
ES = embryonic stem cell-like morphology
AP = alkaline phosphatase activity (positive colonies range from 5% to 60% positive cells)
ES, AP+ corresponds to iPSC state

TABLE 6

Phenotypes of individual cell clones following expansion in respective medium
(Panstra-12)

| Condition | Phenotype | | | |
|---|---|---|---|---|
| | Fl, AP− | Fl, AP+ | ES, AP− | ES, AP+ |
| DFBS, control | 8/21 (38%) | 5/21 (24%) | 8/21 (38%) | 0/21 (0%) |
| DFBS, 1 mM Xn | 12/23 (52%) | 4/23 (17%) | 7/23 (31%) | 0/23 (0%) |
| hiFBS, control | 18/24 (75%) | 0/24 (0%) | 6/24 (25%) | 0/24 (0%) |
| hiFBS, 1 mM Xn | 11/19 (58%) | 0/19 (0%) | 5/19 (26%) | 3/19 (16%) |
| KOSR, control | 4/14 (29%) | 3/14 (21%) | 1/14 (7%) | 6/14 (43%) |
| KOSR, 1 mM Xn | 1/17 (6%) | 1/17 (6%) | 5/17 (29%) | 10/17 (59%) |

Xn effect: p = 0.024
Fl = fibroblast-like morphology
ES = embryonic stem cell-like morphology
AP = alkaline phosphatase activity (positive colonies range from 5% to 90% positive cells)
ES, AP+ corresponds to iPSC state

TABLE 7

Estimated gene-free iPSC colony formation efficiency (%)
(Panstra-12)

| Condition | Phenotype | | | |
|---|---|---|---|---|
| | Fl, AP− | Fl, AP+ | ES, AP− | ES, AP+ |
| DFBS, control | 0.053 | 0.033 | 0.053 | 0.000 |
| DFBS, 1 mM Xn | 0.080 | 0.027 | 0.047 | 0.000 |
| hiFBS, control | 0.120 | 0.000 | 0.040 | 0.000 |
| hiFBS, 1 mM Xn | 0.073 | 0.000 | 0.033 | 0.020 |
| KOSR, control | 0.027 | 0.020 | 0.007 | 0.040 |
| KOSR, 1 mM Xn | 0.007 | 0.007 | 0.033 | 0.067 |

Fl = fibroblast-like morphology
ES = embryonic stem cell-like morphology
AP = alkaline phosphatase activity (positive colonies range from 5% to 90% positive cells)
ES, AP+ corresponds to iPSC state

What is claimed is:

1. A method of reprogramming a population of tissue stem cells comprising the steps of:
 a. contacting a population of cells comprising tissue stem cells with xanthine (Xn) in a culture medium, wherein the tissue stem cells respond to Xn by undergoing symmetric cell division;
 b. culturing the population of cells of step a in the culture medium containing Xn for a sufficient amount of time to expand the number of tissue stem cells by suppression of asymmetric cell kinetics in the presence of Xn; and
 c. culturing the population of cells comprising tissue stem cells from step b in a medium capable of supporting the maintenance of pluripotent cells, thereby reprogramming the cells of step (b) to a pluripotent state.

2. The method of claim 1, wherein Xn is included in the medium capable of supporting the maintenance of pluripotent cells.

3. A method of reprogramming a tissue stem cell comprising the steps of:
 a. clonally isolating a tissue stem cell from a population of cells by culturing the population of cells in a proliferation culture medium comprising xanthine (Xn) to suppress asymmetric kinetics and isolating a tissue stem cell that responds to Xn by undergoing symmetric cell division;
 b. culturing the isolated cell of step a in a proliferation culture medium comprising xanthine for a sufficient time to expand the number of cells by suppression of asymmetric cell kinetics in the presence of Xn; and
 c. culturing the cells of step b) in a medium capable of supporting the maintenance of pluripotent cells thereby reprogramming the tissue stem cell to a pluripotent state.

4. The method of claims 3, wherein the medium capable of supporting the maintenance of pluripotent cells comprises Xn.

5. The method of claim 1, wherein the concentration of xanthine is about 1 mM.

6. The method of claim 1, wherein the tissue stem cell is selected from the group of liver stem cells, hair follicle stem cells and pancreas stem cells.

7. A method of reprogramming a tissue stem cell comprising contacting a tissue stem cell with xanthine in a medium capable of supporting the maintenance of pluripotent cells, wherein the tissue stem cell responds to Xn by undergoing symmetric cell division.

8. The method of claim 7, wherein the concentration of xanthine is about 1 mM.

9. The method of claim 7, wherein the tissue stem cell is selected from the group of liver stem cells, hair follicle stem cells and pancreas stem cells.

* * * * *